US008679030B2

(12) United States Patent
Shinar et al.

(10) Patent No.: US 8,679,030 B2
(45) Date of Patent: Mar. 25, 2014

(54) MONITORING A CONDITION OF A SUBJECT

(71) Applicant: EarlySense Ltd, Ramat Gan (IL)

(72) Inventors: Zvika Shinar, Binyamina (IL); Guy Meger, Haifa (IL); Avner Halperin, Ramat Gan (IL); Daniel H. Lange, Kfar Vradim (IL)

(73) Assignee: EarlySense Ltd., Ramat Gan (IL)

( * ) Notice: Subject to any disclaimer, the term of this patent is extended or adjusted under 35 U.S.C. 154(b) by 0 days.

(21) Appl. No.: 13/921,915

(22) Filed: Jun. 19, 2013

(65) Prior Publication Data

US 2013/0281866 A1 Oct. 24, 2013

Related U.S. Application Data

(63) Continuation of application No. 13/107,772, filed on May 13, 2011, now Pat. No. 8,491,492, which is a continuation-in-part of application No. 11/552,872, filed on Oct. 25, 2006, and a continuation-in-part of application No. 11/782,750, filed on Jul. 25, 2007, now Pat. No. 8,403,865, which is a continuation-in-part of application No. 11/446,281, filed on Jun. 2, 2006, now Pat. No. 8,376,954, which is a continuation of application No. 11/048,100, filed on Jan. 31, 2005, now Pat. No. 7,077,810, said application No. 11/782,750 is a continuation-in-part of application No. 11/197,786, filed on Aug. 3, 2005, now Pat. No. 7,314,451.

(60) Provisional application No. 60/731,934, filed on Nov. 1, 2005, provisional application No. 60/784,799, filed on Mar. 23, 2006, provisional application No. 60/843,672, filed on Sep. 12, 2006, provisional application No. 60/541,779, filed on Feb. 5, 2004, provisional application No. 60/674,382, filed on Apr. 25, 2005, provisional application No. 60/692,105, filed on Jun. 21, 2005.

(51) Int. Cl.
| | | |
|---|---|---|
| A61B 5/08 | (2006.01) | |
| A61B 5/02 | (2006.01) | |
| A61B 5/00 | (2006.01) | |
| A61N 1/362 | (2006.01) | |

(52) U.S. Cl.
USPC .............. 600/534; 600/16; 600/301; 600/483

(58) Field of Classification Search
USPC ................... 600/16, 301, 483, 534
See application file for complete search history.

(56) References Cited

U.S. PATENT DOCUMENTS 3,890,958 A 6/1975 Fister et al.
4,122,838 A 10/1978 Leonard
(Continued)

FOREIGN PATENT DOCUMENTS

EP 0853918 7/1998
EP 0860803 8/1998
(Continued)

OTHER PUBLICATIONS

Shochat, Michael et al., "PedemaTOR: Innovative method for detecting pulmonary edema at the pre-clinical stage", http://www.isramed.info/rsmn_rabinovich/pedemator.htm.

(Continued)

Primary Examiner — Nicole F Lavert
(74) Attorney, Agent, or Firm — Rodney J. Fuller; Booth Udall Fuller, PLC

(57) ABSTRACT

A method of predicting an onset of apnea is described. Motion of a subject, including at least breathing-related motion, is sensed, and a signal corresponding to the sensed motion is generated. A breathing-related signal is extracted from the sensed motion signal, and the onset of apnea is predicted at least partially in response to analyzing the breathing-related signal. Other applications are also described.

19 Claims, 9 Drawing Sheets

(56) References Cited

U.S. PATENT DOCUMENTS

| | | |
|---|---|---|
| 4,301,879 A | 11/1981 | Dubow |
| 4,338,950 A | 7/1982 | Barlow, Jr. |
| 4,494,553 A | 1/1985 | Sciarra |
| 4,657,025 A | 4/1987 | Orlando |
| 4,657,026 A | 4/1987 | Tagg |
| 4,686,999 A | 8/1987 | Snyder |
| 4,738,264 A | 4/1988 | Orlando |
| 4,757,825 A | 7/1988 | Diamond |
| 4,817,610 A | 4/1989 | Lee |
| 4,926,866 A | 5/1990 | Lee |
| 5,002,060 A | 3/1991 | Nedivi |
| 5,010,772 A | 4/1991 | Bourland |
| 5,025,791 A | 6/1991 | Niwa |
| 5,076,281 A | 12/1991 | Gavish |
| 5,107,845 A | 4/1992 | Guern |
| 5,111,826 A | 5/1992 | Nasiff |
| 5,137,033 A | 8/1992 | Norton |
| 5,235,989 A | 8/1993 | Zomer |
| 5,253,656 A | 10/1993 | Rincoe |
| 5,276,432 A | 1/1994 | Travis |
| 5,309,921 A | 5/1994 | Kisner |
| 5,309,922 A | 5/1994 | Schechter |
| 5,319,363 A | 6/1994 | Welch |
| 5,368,026 A | 11/1994 | Swedlow |
| 5,393,935 A | 2/1995 | Hasty |
| 5,448,996 A | 9/1995 | Bellin et al. |
| 5,479,939 A | 1/1996 | Ogino |
| 5,515,865 A | 5/1996 | Scanlon |
| 5,520,176 A | 5/1996 | Cohen |
| 5,522,382 A | 6/1996 | Sullivan |
| 5,540,734 A | 7/1996 | Zabara |
| 5,590,650 A | 1/1997 | Genova |
| 5,620,003 A | 4/1997 | Sepponen |
| 5,662,106 A | 9/1997 | Swedlow |
| 5,684,460 A | 11/1997 | Scanlon |
| 5,687,734 A | 11/1997 | Dempsey |
| 5,699,038 A | 12/1997 | Ulrich |
| 5,730,140 A | 3/1998 | Fitch |
| 5,738,102 A | 4/1998 | Lemelson |
| 5,743,263 A | 4/1998 | Baker, Jr. |
| 5,797,852 A | 8/1998 | Karakasoglu |
| 5,800,337 A | 9/1998 | Gavish |
| 5,800,360 A | 9/1998 | Kisner |
| 5,853,005 A | 12/1998 | Scanlon |
| 5,879,313 A | 3/1999 | Raviv |
| 5,902,250 A | 5/1999 | Verrier |
| 5,944,680 A | 8/1999 | Christopherson |
| 5,957,861 A | 9/1999 | Combs |
| 5,964,720 A | 10/1999 | Pelz |
| 5,989,193 A | 11/1999 | Sullivan |
| 6,014,346 A | 1/2000 | Malone |
| 6,015,388 A | 1/2000 | Sackner |
| 6,033,370 A | 3/2000 | Reinbold |
| 6,036,660 A | 3/2000 | Toms |
| 6,047,203 A | 4/2000 | Sackner |
| 6,062,216 A | 5/2000 | Corn |
| 6,064,910 A | 5/2000 | Andersson |
| 6,080,106 A | 6/2000 | Lloyd |
| 6,090,037 A | 7/2000 | Gavish |
| 6,093,146 A | 7/2000 | Filangeri |
| 6,104,949 A | 8/2000 | Pitts Crick |
| 6,126,595 A | 10/2000 | Amano |
| 6,134,970 A | 10/2000 | Kumakawa |
| 6,135,970 A | 10/2000 | Kadhiresan |
| 6,157,850 A | 12/2000 | Diab |
| 6,168,568 B1 | 1/2001 | Gavriely |
| 6,198,394 B1 | 3/2001 | Jacobsen |
| 6,223,064 B1 | 4/2001 | Lynn |
| 6,239,706 B1 | 5/2001 | Yoshiike |
| 6,259,355 B1 | 7/2001 | Chaco |
| 6,261,238 B1 | 7/2001 | Gavriely |
| 6,290,654 B1 | 9/2001 | Karakasoglu |
| 6,325,761 B1 | 12/2001 | Jay |
| 6,352,517 B1 | 3/2002 | Flock |
| 6,368,287 B1 | 4/2002 | Hadas |
| 6,375,621 B1 | 4/2002 | Sullivan |
| 6,375,623 B1 | 4/2002 | Gavriely |
| 6,383,142 B1 | 5/2002 | Gavriely |
| 6,402,691 B1 | 6/2002 | Peddicord |
| 6,409,661 B1 | 6/2002 | Murphy |
| 6,436,057 B1 | 8/2002 | Goldsmith |
| 6,450,957 B1 | 9/2002 | Yoshimi |
| 6,454,719 B1 | 9/2002 | Greenhut |
| 6,468,234 B1 | 10/2002 | Van der Loos |
| 6,485,441 B2 | 11/2002 | Woodward |
| 6,498,652 B1 | 12/2002 | Varshneya |
| 6,512,949 B1 | 1/2003 | Combs |
| 6,517,497 B2 | 2/2003 | Rymut |
| 6,527,729 B1 | 3/2003 | Turcott |
| 6,544,173 B2 | 4/2003 | West |
| 6,544,174 B2 | 4/2003 | West |
| 6,547,743 B2 | 4/2003 | Brydon |
| 6,551,252 B2 | 4/2003 | Sackner |
| 6,561,978 B1 | 5/2003 | Conn |
| 6,579,232 B2 | 6/2003 | Sakamaki |
| 6,585,645 B2 | 7/2003 | Hutchinson |
| 6,589,188 B1 | 7/2003 | Street |
| 6,599,251 B2 | 7/2003 | Chen |
| 6,600,949 B1 | 7/2003 | Turcott |
| 6,616,606 B1 | 9/2003 | Petersen |
| 6,630,568 B1 | 10/2003 | Johnson |
| 6,631,281 B1 | 10/2003 | Kastle |
| 6,641,542 B2 | 11/2003 | Cho |
| 6,646,556 B1 | 11/2003 | Smith |
| 6,662,032 B1 | 12/2003 | Gavish |
| 6,666,830 B1 | 12/2003 | Lehrman |
| 6,719,708 B1 | 4/2004 | Jansen |
| 6,725,074 B1 | 4/2004 | Kastle |
| 6,731,311 B2 | 5/2004 | Bufe |
| 6,745,060 B2 | 6/2004 | Diab |
| 6,751,498 B1 | 6/2004 | Greenberg |
| 6,752,766 B2 | 6/2004 | Kowallik |
| 6,754,516 B2 | 6/2004 | Mannheimer |
| 6,790,183 B2 | 9/2004 | Murphy |
| 6,821,258 B2 | 11/2004 | Reed |
| 6,822,564 B2 | 11/2004 | Al-Ali |
| 6,827,670 B1 | 12/2004 | Stark |
| 6,830,548 B2 | 12/2004 | Bonnet |
| 6,840,907 B1 | 1/2005 | Brydon |
| 6,856,141 B2 | 2/2005 | Ariav |
| 6,878,121 B2 | 4/2005 | Krausman |
| 6,893,404 B2 | 5/2005 | Ragnarsdottir |
| 6,955,647 B2 | 10/2005 | Rice |
| 6,980,679 B2 | 12/2005 | Jeung |
| 6,984,207 B1 | 1/2006 | Sullivan |
| 6,984,993 B2 | 1/2006 | Ariav |
| 6,988,989 B2 | 1/2006 | Weiner |
| 7,022,072 B2 | 4/2006 | Fox |
| 7,025,729 B2 | 4/2006 | de Chazal |
| 7,077,810 B2 | 7/2006 | Lange |
| 7,079,035 B2 | 7/2006 | Bock |
| 7,283,161 B2 | 10/2007 | Someya |
| 7,304,580 B2 | 12/2007 | Sullivan |
| 7,314,451 B2 | 1/2008 | Halperin |
| 7,390,299 B2 | 6/2008 | Weiner |
| 7,396,331 B2 | 7/2008 | Mack |
| 7,396,333 B2 | 7/2008 | Stahmann |
| 7,415,297 B2 | 8/2008 | Al-Ali |
| 7,428,468 B2 | 9/2008 | Takemura |
| 7,431,700 B2 | 10/2008 | Aoki |
| 7,433,827 B2 | 10/2008 | Rosenfeld |
| 7,439,856 B2 | 10/2008 | Weiner |
| 7,454,359 B2 | 11/2008 | Rosenfeld |
| 7,508,307 B2 | 3/2009 | Albert |
| 7,572,225 B2 | 8/2009 | Stahmann |
| 7,610,094 B2 | 10/2009 | Stahmann |
| 7,629,890 B2 | 12/2009 | Sullivan |
| 7,666,151 B2 | 2/2010 | Sullivan |
| 7,689,440 B2 | 3/2010 | Brown |
| 7,704,215 B2 | 4/2010 | Lewicke |
| 7,778,851 B2 | 8/2010 | Schoenberg |
| 7,860,583 B2 | 12/2010 | Condurso |
| 7,880,606 B2 | 2/2011 | Al-Ali |
| 7,896,813 B2 | 3/2011 | Sowelam |

(56) References Cited

U.S. PATENT DOCUMENTS

| | | |
|---|---|---|
| 7,938,782 B2 | 5/2011 | Stahmann |
| 7,952,475 B2 | 5/2011 | Ivanov |
| 7,959,574 B2 | 6/2011 | Bardy |
| 8,016,480 B2 | 9/2011 | Lozinski |
| 8,376,954 B2 | 2/2013 | Lange |
| 8,403,865 B2 | 3/2013 | Halperin |
| 2001/0005773 A1 | 6/2001 | Larsen |
| 2002/0058155 A1 | 5/2002 | Guofang |
| 2002/0077554 A1 | 6/2002 | Schwartz |
| 2002/0082486 A1 | 6/2002 | Lavery |
| 2002/0086870 A1 | 7/2002 | Radulovacki |
| 2002/0097155 A1 | 7/2002 | Cassel |
| 2002/0099303 A1 | 7/2002 | Bardy |
| 2002/0106709 A1 | 8/2002 | Potts |
| 2002/0196148 A1 | 12/2002 | Nunome |
| 2003/0004403 A1 | 1/2003 | Drinan |
| 2003/0004423 A1 | 1/2003 | Lavie |
| 2003/0045806 A1 | 3/2003 | Brydon |
| 2003/0125612 A1 | 7/2003 | Fox |
| 2003/0135127 A1 | 7/2003 | Sackner |
| 2003/0139678 A1 | 7/2003 | Hoium |
| 2003/0144829 A1 | 7/2003 | Geatz |
| 2003/0153831 A1 | 8/2003 | Zumeris |
| 2003/0199945 A1 | 10/2003 | Ciulla |
| 2004/0010202 A1 | 1/2004 | Nakatani |
| 2004/0073098 A1 | 4/2004 | Geva |
| 2004/0082874 A1 | 4/2004 | Aoki |
| 2004/0111040 A1 | 6/2004 | Ni |
| 2004/0111045 A1 | 6/2004 | Sullivan |
| 2004/0116784 A1 | 6/2004 | Gavish |
| 2004/0133079 A1 | 7/2004 | Mazar |
| 2004/0210155 A1 | 10/2004 | Takemura |
| 2004/0225226 A1 | 11/2004 | Lehrman |
| 2004/0230105 A1 | 11/2004 | Geva |
| 2005/0027216 A1 | 2/2005 | Guillemaud |
| 2005/0043644 A1 | 2/2005 | Stahmann |
| 2005/0061315 A1 | 3/2005 | Lee |
| 2005/0074361 A1 | 4/2005 | Tanoshima |
| 2005/0080349 A1 | 4/2005 | Okada |
| 2005/0085734 A1 | 4/2005 | Tehrani |
| 2005/0085866 A1 | 4/2005 | Tehrani |
| 2005/0096557 A1 | 5/2005 | Vosburgh |
| 2005/0119586 A1 | 6/2005 | Coyle |
| 2005/0124864 A1 | 6/2005 | Mack |
| 2005/0165284 A1 | 7/2005 | Gefen |
| 2005/0168341 A1 | 8/2005 | Reeder |
| 2005/0192508 A1 | 9/2005 | Lange |
| 2005/0201970 A1 | 9/2005 | Hu |
| 2005/0240091 A1 | 10/2005 | Lynn |
| 2006/0028350 A1 | 2/2006 | Bhai |
| 2006/0063982 A1 | 3/2006 | Sullivan |
| 2006/0084848 A1 | 4/2006 | Mitchnick |
| 2006/0089856 A1 | 4/2006 | Kadhiresan |
| 2006/0129047 A1 | 6/2006 | Ruotoistenmaki |
| 2006/0152378 A1 | 7/2006 | Lokhorst |
| 2006/0195025 A1 | 8/2006 | Ali |
| 2006/0220885 A1 | 10/2006 | Bock |
| 2006/0241510 A1 | 10/2006 | Halperin |
| 2006/0258952 A1 | 11/2006 | Stahmann |
| 2007/0024451 A1 | 2/2007 | Albert |
| 2007/0032733 A1 | 2/2007 | Burton |
| 2007/0118054 A1 | 5/2007 | Pinhas |
| 2007/0139678 A1 | 6/2007 | Horita |
| 2007/0156031 A1 | 7/2007 | Sullivan |
| 2007/0177785 A1 | 8/2007 | Raffy |
| 2007/0249952 A1 | 10/2007 | Rubin |
| 2007/0257564 A1 | 11/2007 | Kitade |
| 2007/0276202 A1 | 11/2007 | Raisanen |
| 2008/0004904 A1 | 1/2008 | Tran |
| 2008/0005838 A1 | 1/2008 | Wan Fong |
| 2008/0114260 A1 | 5/2008 | Lange |
| 2008/0275349 A1 | 11/2008 | Halperin |
| 2009/0164239 A1 | 6/2009 | Hayter |
| 2009/0299229 A1 | 12/2009 | Johnson |
| 2010/0217618 A1 | 8/2010 | Piccirillo |
| 2010/0234705 A1 | 9/2010 | Lynn |
| 2011/0046498 A1 | 2/2011 | Klap |
| 2011/0112442 A1 | 5/2011 | Meger |
| 2011/0282216 A1 | 11/2011 | Shinar |
| 2012/0253142 A1 | 10/2012 | Meger |
| 2013/0174345 A1 | 7/2013 | Leu |

FOREIGN PATENT DOCUMENTS

| | | |
|---|---|---|
| GB | 2329966 | 4/1999 |
| JP | 5323635 | 12/1993 |
| JP | 08-080285 | 3/1996 |
| JP | 08-225210 | 9/1996 |
| JP | 2001-037739 | 2/2001 |
| JP | 2001-145605 | 5/2001 |
| JP | 2001-327549 | 11/2001 |
| JP | 2002-336207 | 11/2002 |
| JP | 2004-049388 | 2/2004 |
| JP | 2005-021450 | 1/2005 |
| JP | 2005-095307 | 4/2005 |
| JP | 2005-143661 | 6/2005 |
| JP | 2005-160876 | 6/2005 |
| JP | 2005-237479 | 9/2005 |
| JP | 2005-279113 | 10/2005 |
| WO | 86/05965 | 10/1986 |
| WO | 96/08197 | 3/1996 |
| WO | 97/40748 | 11/1997 |
| WO | 99/04691 | 2/1999 |
| WO | 99/32537 | 7/1999 |
| WO | 01/73718 | 10/2001 |
| WO | 01/80727 | 11/2001 |
| WO | 03/013355 | 2/2003 |
| WO | 03/057025 | 7/2003 |
| WO | 2004/006768 | 1/2004 |
| WO | 2004/091378 | 10/2004 |
| WO | 2004/114193 | 12/2004 |
| WO | 2005/028029 | 3/2005 |
| WO | 2005/037077 | 4/2005 |
| WO | 2005/037366 | 4/2005 |
| WO | 2005/055824 | 6/2005 |
| WO | 2005/074361 | 8/2005 |
| WO | 2006/008743 | 1/2006 |
| WO | 2006/054306 | 5/2006 |
| WO | 2006/082589 | 8/2006 |
| WO | 2006/137067 | 12/2006 |
| WO | 2007/052108 | 5/2007 |
| WO | 2007/081629 | 7/2007 |
| WO | 2008/135985 | 11/2008 |
| WO | 2009/138976 | 11/2009 |
| WO | 2012/077113 | 6/2012 |

OTHER PUBLICATIONS

Sorvoja, H. and Myllyla, R., "Noninvasive blood pressure measurement methods," Molecular and Quantum Acoustics. vol. 27, 2006.

Staderini, Enrico M., (2002) UWB Radars in Medicine, IEEE Aerospace and Electronic Systems Magazine, 17(1):13-18.

Stegmaier-Stracca, Peter A. et al., Cough detection using fuzzy classification, Proceeding of the 1995 ACM Symposium on Applied Computing, Nashville, TN: 440-4.

Tamura T. et al., "A system for monitoring temperature distribution in bed and its application to the assessment of body movement", Physiological Measurement, Institute of Physics Publishing, Bristol, GB 1993; 14(1): 33-41.

Thorpe C.W. et al., (1992) "Towards a quantitative description of asthmatic cough sounds", Eur Respir J 5(6):685-92.

Van Der Loos, H.F. Michiel et al., "Unobstrusive vital signs monitoring from a multisensory bed sheet", RESNA 2001, Reno, NV, Jun. 22-26, 2001, pp. 218-220.

Van Der Loos, H.F.M. et al., "Development of sensate and robotic bed technologies for vital signs monitoring and sleep quality improvement", Abstract, Autonomous Robots, 2003;15(1) http://www.ingenta.com/isi/searching/Expand/ingenta?pub=infobike://klu/auro/2003/00000015/00000001/05126829.

Van Hirtum A. et al., (2002) Autoregressive acoustical modeling of free field cough sound, Proc Int Conference on Acoustics, Speech and Signal Processing, col. 1, pp. 493-496, Orlando, USA.

(56) References Cited

OTHER PUBLICATIONS

Waris, M. et al., "A new method for automatic wheeze detection", Technology and Health Care 1998; 6:33-40.
Watanabe et al., (2004) "Noncontact method for sleep stage estimation", IEEE transactions on Biomedical Engineering 10(51):1735-48.
Whitney, C.W., Gottlieb DJ, Redline S, Norman RG, Dodge RR, Shahar E, Surovec S and Nieto FJ, "Reliability of scoring respiratory disturbance indices and sleep staging," Sleep, Nov. 2, 1998; 21(7): 749-757.
Yien HW et al., (1997) Spectral analysis of systemic arterial pressure and heart rate signals as a prognostic tool for the prediction of patient outcome in the intensive care unit. Crit Care Med. 25(2):258-66.
Yongjoon et al., (2005) "Air mattress sensor system with balancing tube for unconstrained measurement of respiration and heart beat movements", Physiol Meas, pp. 413-422.
"Breathing easier with astma", pp. 1-46, http://www.ihc.com/xp/ihc/documents/clinica1/101/3/1/asthma_breathe.;pdf (2003).
"British guidelines on management of asthma: a national clinical guidline", British Thoracic Society, Scottish Intercollegiate Guidelines Network, Revised edition, Apr. 2004, pp. 1-92.
"Does my child have asthma?" Solano Asthma Coalition, American Lung Association of the East Bay (http://www.alaebay.org/misc_pdf/solano_asthma_coalition_child_asthma.pdf) (2001).
"Managing asthma", http://kidshealth.org/pageManager.jsp?dn=KidsHealth&lic=1&ps=107&cat_id=143&article_set=2 (Aug. 2011).
"Medical Mutual clinical practice guidelines for asthma: 2004," Medical Mutual (Cleveland, OH), (http://www.medmutual.com/provider/pdf/resources/asthma4.pdf).
"Non-invasive fiber-optic sensor technology for monitoring sleep apnea and SIDS", http://www.kidsource.com/products/fiber.optic.SIDS.html (Retrieved Apr. 18, 2005).
"Peak flow learning center", http://www.njc.org/disease-info/diseases/asthma/living/tools/peak/index/aspx (Retrieved Feb. 22, 2007).
"Signs and symptoms of asthma", http://www.indianchestsociety.org/symptomsofasthma.htm (Retrieved Feb. 22, 2007).
Alihanka, J. et al., "A new method for long-term monitoring ballistocardiogram, heart rate, and respiration", AM J Physiol Regul Integ Comp Physiol 1981; 240: 384-92.
Alihanka, J. et al., "A static charge sensitive bed. A new method for recording body movement during sleep", Electroencephalography and Clinical Neurophysiology 1979; 46(6): 731-4.
Ancoli-Israel S. et al., (2003) The role of actigraphy in the study of sleep and circadian rhythms. Sleep. 26(3):342-92.
Baren, Jill M. et al., "Current Concepts in the ED treatment of pediatric Asthma", Respiratory Medicine Consensus Reports (Thomson American Health Consultants, Dec. 28, 2003), pp. 1-12.
Bentur, L. et al., "Wheeze monitoring in children for assessment of nocturnal asthma and response to therapy", Eur respire J 2003; 21: 621-6.
Bilmes et al., (1998) A gentle tutorial of the EM algorithm and its application to parameter estimation for caussian mixture and hidden markov models. Internation Computer Science Institut, pp. 1-13.
Brenner, Barry E. et al., "The clinical presentation of acute ashma in adults and children", In Brenner, BE, ed. Emergency Asthma (New York: Marcel Dekker 1994; pp. 201-232).
Butter CD. et al., (1978) Fiber optics strain gauge. Appl Opt. 17(18): 2867-9.
Chaboyer W et al., (2008) Predictors of adverse events in patients after discharge from the intensive care unit. Am J Crit Care. 17:255-63.
Chan et al., Prosafe a multisensory remote monitoring system for the elderly or the handicapped, Independent Living for Persons with Disabilities and Elderly People: ICOST, 2003 1st International Conference on Smart Homes and Health Telematics.
Chang, A.B. et al., "Cough, airway inflammation, and mild asthma exacerbation", Archives of disease in childhood 2002; 86:270-5.

Delmore G. et al., (1977) The role of augmented breaths (sighs) in bronchial asthma attacks. Pflugers Arch. 372(1):1-6.
Dempster AP. et al., (1977) Maximum likelihood from incomplete data via the EM algorithm. Ournal of the Royal statistical Society 39(1):1-38.
E. Campo, M. Chan, Detecting abnormal behaviour by real-time monitoring of patients, AAAI Technical Report WS-02-02. Compilation copyright © 2002.
Fieselmann JF et al., (1993) Respiratory rate predicts cardiopulmonary arrest for internal medicine inpatients. J Gen Intern Med 8(7):354-60.
Fitzpatrick MF. et al., (1991) Morbidity in nocturnal asthma: sleep quality and daytime cognitive performance. Thorax. 46(8):569-73.
Fitzpatrick, MF. et al., (1993) "Snoring, asthma and sleep distrurbances in Britain: a community based survey", ERS Journal Ltd., pp. 531-535.
Hark et al., (2005) Spontaneous sigh rates during sedentary activity: watching television vs reading. Ann Allergy Asthma Immunol. 94(2):247-50.
Hogan J., (2006) Why don't nurses monitor the respiratory rates of patients? Br J Nurs 15(9):489-92.
Hori et al., (2001) Proposed supplements and amendments to 'A Manual of Standardized Terminology, Techniques and Scoring System for Sleep Stages of Human Subjects', the Rechtschaffen & Kales (1968) standard. Psychiatry Clin Neurosci. 55(3):305-10.
Hsu, J.Y. et al., "Coughing frequency in patients with persistent cough; Assessment using a 24 hour ambulatory recorder", Eur Repir J 1994; 7: 1246-53.
Hudgel et al., (1984) Mechanics of the respiratory system and breathing pattern during sleep in normal humans. J Appl Physiol. 56(1): 133-7.
Jobanputra et al., (1991) Management of acute asthma attacks in general practice. Br J Gen Pract. Oct. 1991;41 (351):410-3.
Kandtelhardt, J.W., T. Penzel, S. Rostig, H. F. Becker, S. Halvin, and A. Bunde, Breathing during REM and non-REM sleep: correlated versus uncorrelated behavior, 25 Physica. A., vol. 319, pp. 447-457, 2003.
Kap-Ho Seo et al., "Bed-type robotic system for the bedridden", advanced Intelligent Mechatronics, Proceedings, 2005 IEE/ASME International Conference on Monterey, CA Jul. 24-28, 2005. Piscataway, NK, USA pp. 1170-1175.
Kapsali et al., "Potent bronchoprotective effect of deep inspiration and its absence in asthma", J Appl Physiol., 89(2):711-720 (2000).
Katz et al., (1986) Detection of preterm labor by ambulatory monitoring of uterine activity: a preliminary report. Obstet Gynecol. Dec. 1986;68(6): 773-8.
Korpas, J. et al., "Analysis of the cough sound: an overview", Pulmonary Pharmacology 1996; 9: 261-8.
Li, Q. and A. Barron, "Mixture density estimation," Advances in neural information processing systems, vol. 12, pp. 279-285, MIT press, 2000.
Lim TO. et al., (1992) Morbidity associated with asthma and audit of asthma treatment in out-patient clinics. Singapore Med J. 33(2):174-6.
Mack, David et al., "Non-invasive analysis of physiological signals: NAPS: A low cost, passive monitoring for sleep quality and related applications", University of Virginia Health System. pp. 1-9 (Oct. 2002).
Madge PJ et al., (1995) Home nebuliser use in children with asthma in two Scottish Health Board Areas. Scott Med J. 40(5):141-3.
Mintzer, Rich, "What the teacher should know about asthma attacks", http://www.familyeducation.com/article/print/0,1303,65-415,00.html?obj_gra (Retrieved Feb. 22, 2007).
O'Connor CJ et al, "Identification of endotracheal tube malpositions using computerized analysis of breath sounds via electronic stethoscopes," Anesth Analg 2005;101:735-9.
Oppenheim, AN., and R.W. Schafer, Discrete-Time Signal Processing, Prentice' Hall, 1989, pp. 311-312.
Pirrila, P. et al., "Objective assessment of cough", Eur respire J 1995; 8: 1949-56.
Plaut, Thomas F., "Tracking and treating asthma in young children", J Respir Dis Pediatrician 2003; 5(2): 67-72.

(56) References Cited

OTHER PUBLICATIONS

Poteet, Jackie, "Asthma". http://www.nku.edu/~rad350/asthmajp.html (Retrieved Jun. 25, 2012).

Salmi et al., (1986) "Automatic analysis of sleep records with static charge sensitive bed", Electroencephalography and Clinical Neurophysiology, pp. 84-87.

Salmi, Tapani et al., "Long-term recording and automatic analysis of cough using filtered acoustic signals and movements on static charge sensitive bed", Chest 1988; 94: 970-5.

Schwartz, (1978) Estimating the dimension of a model. The Annals of Statistics 6(2):461-4.

Shinar Z. et al., (2001) Automatic detection of flow-wave-sleep using heart rate variability. Computers in cardiology 28:593-6.

International Search Report for PCT/IL2013/050283 dated Aug. 28, 2013.

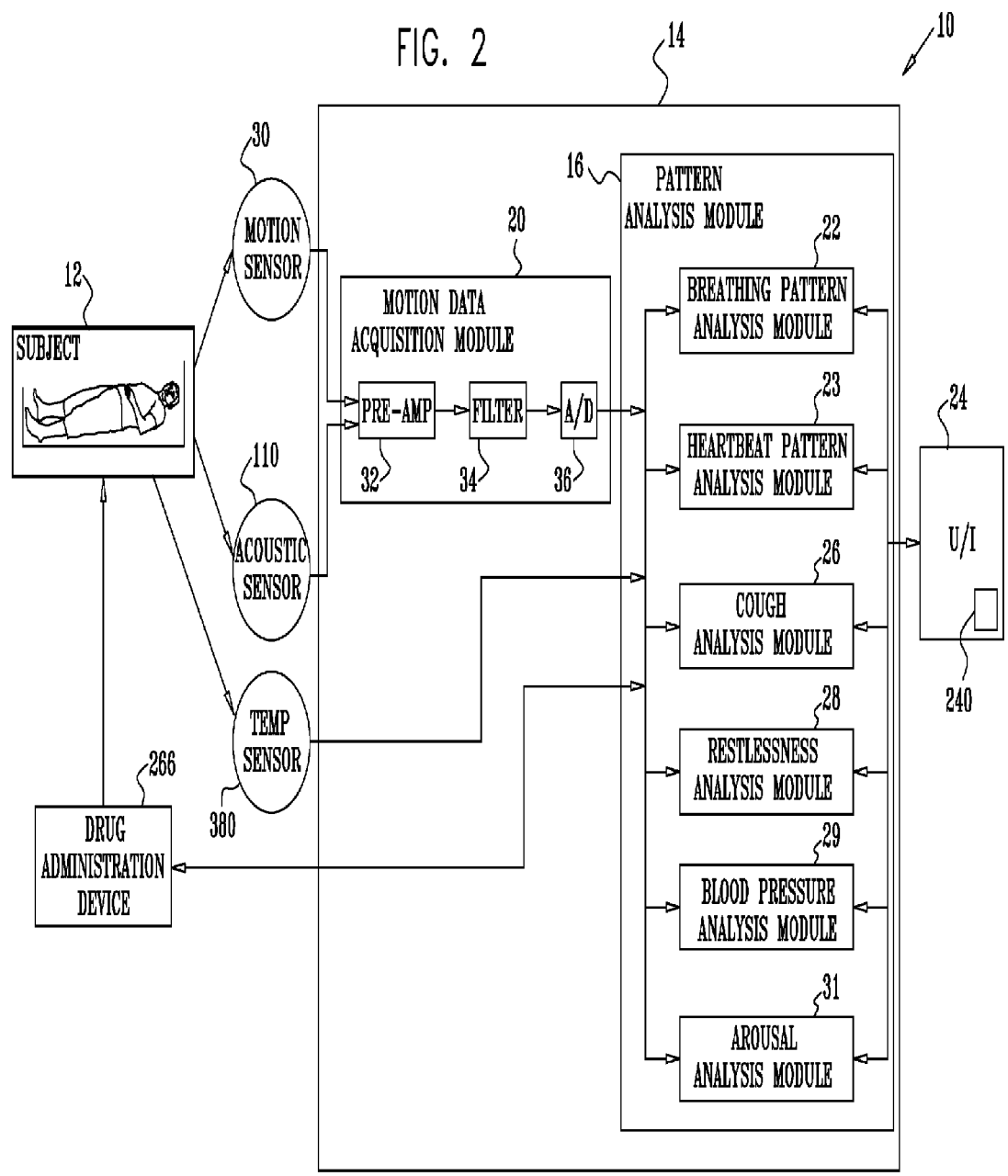

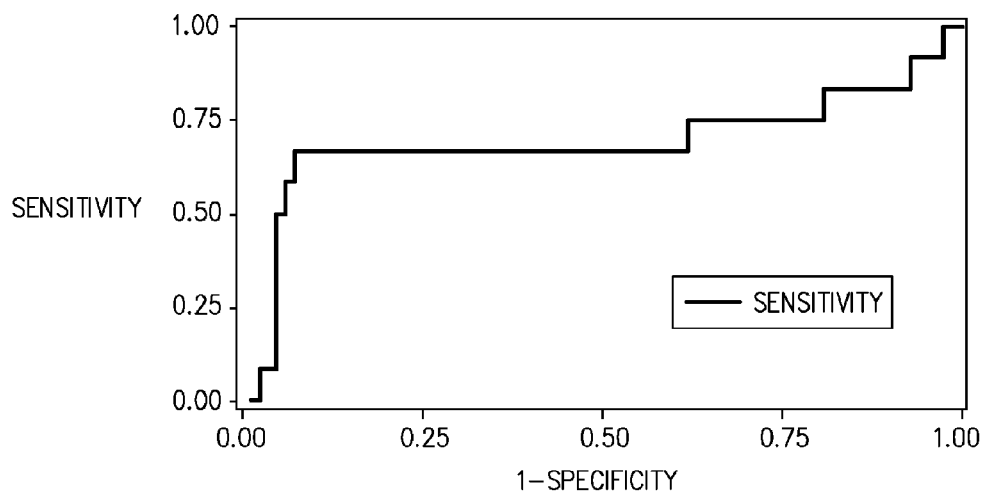
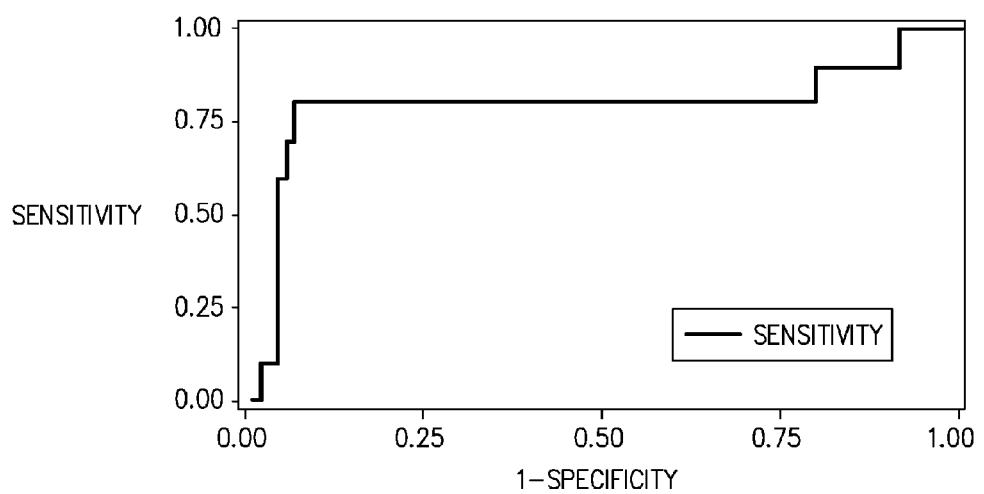

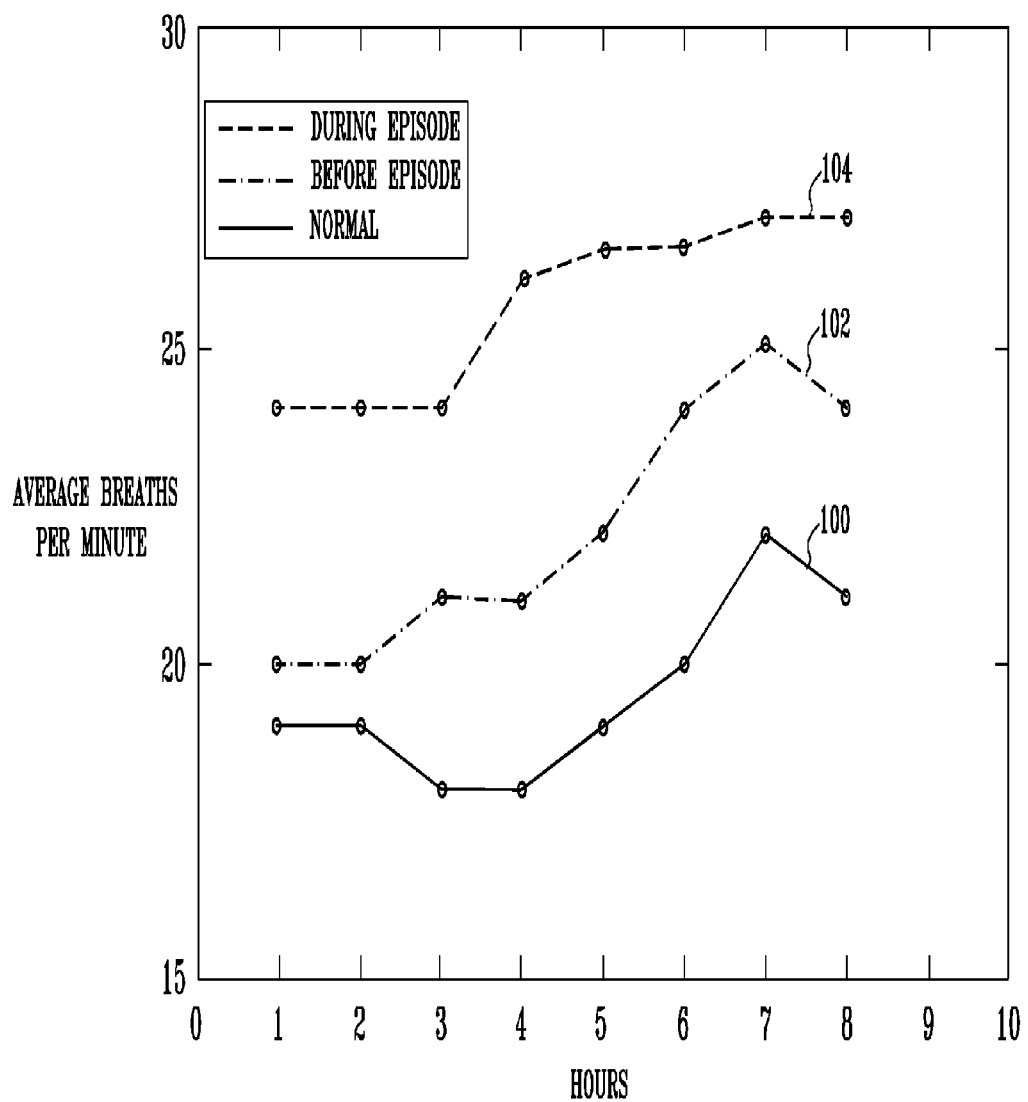

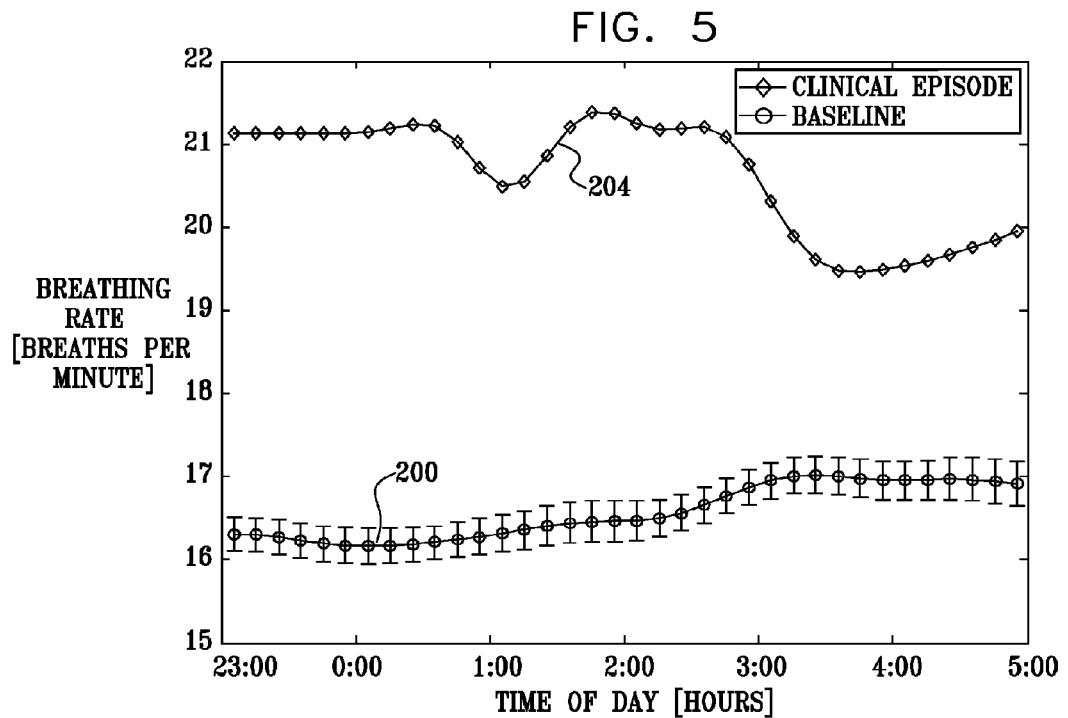
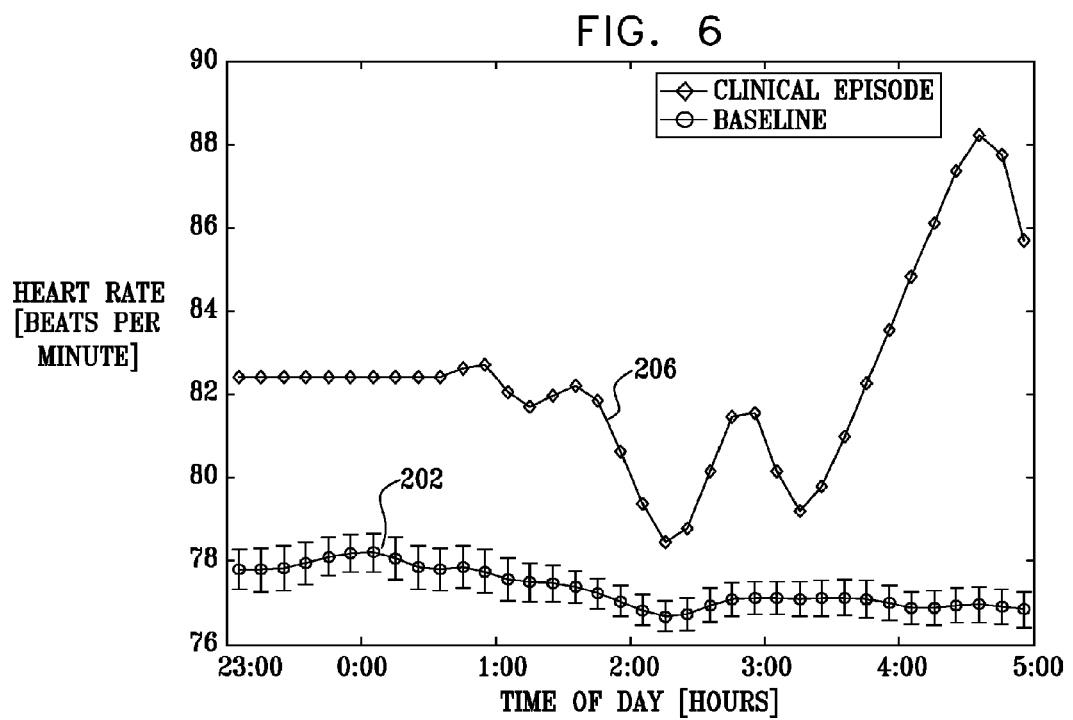

MONITORING A CONDITION OF A SUBJECT

CROSS-REFERENCES TO RELATED APPLICATIONS

The present application is a continuation of U.S. patent application Ser. No. 13/107,772 to Shinar (now U.S. Pat. No. 8,491,492), filed May 13, 2011, which:

is a continuation-in-part of U.S. patent application Ser. No. 11/552,872 to Pinhas (published as U.S. 2007/0118054), filed Oct. 25, 2006, which claims the benefit of (a) U.S. Provisional Patent Application 60/731,934 to Halperin, filed Nov. 1, 2005, (b) U.S. Provisional Patent Application 60/784,799 to Halperin filed Mar. 23, 2006, and (c) U.S. Provisional Patent Application 60/843,672 to Halperin, filed Sep. 12, 2006; and is a continuation-in-part of U.S. patent application Ser. No. 11/782,750 to Halperin (now U.S. Pat. No. 8,403,865), filed Jul. 25, 2007.

All of the above-mentioned applications are incorporated herein by reference.

FIELD OF EMBODIMENTS OF THE INVENTION

Some applications of the present invention relate generally to predicting and monitoring physiological conditions. Specifically, some applications relate to methods and apparatus for monitoring a subject by monitoring the subject's respiration rate and/or the subject's heart rate.

BACKGROUND

Chronic diseases are often expressed by episodic worsening of clinical symptoms. Preventive treatment of chronic diseases reduces the overall dosage of required medication and associated side effects, and lowers mortality and morbidity. Generally, preventive treatment should be initiated or intensified as soon as the earliest clinical symptoms are detected, in order to prevent progression and worsening of the clinical episode and to stop and reverse the pathophysiological process. Therefore, the ability to accurately monitor pre-episodic indicators increases the effectiveness of preventive treatment of chronic diseases.

Many chronic diseases cause systemic changes in vital signs, such as breathing and heartbeat patterns, through a variety of physiological mechanisms. For example, common respiratory disorders, such as asthma, chronic obstructive pulmonary disease (COPD), and cystic fibrosis (CF), are direct modifiers of breathing and/or heartbeat patterns. Other chronic diseases, such as diabetes, epilepsy, and certain heart conditions (e.g., congestive heart failure (CHF)), are also known to modify cardiac and breathing activity. In the case of certain heart conditions, such modifications typically occur because of pathophysiologies related to fluid retention and general cardiovascular insufficiency. Other signs such as coughing and sleep restlessness are also known to be of importance in some clinical situations.

Many chronic diseases induce systemic effects on vital signs. For example, some chronic diseases interfere with normal breathing and cardiac processes during wakefulness and sleep, causing abnormal breathing and heartbeat patterns.

Breathing and heartbeat patterns may be modified via various direct and indirect physiological mechanisms, resulting in abnormal patterns related to the cause of modification. Some respiratory diseases, such as asthma, and some heart conditions, such as CHF, are direct breathing modifiers. Other metabolic abnormalities, such as hypoglycemia and other neurological pathologies affecting autonomic nervous system activity, are indirect breathing modifiers.

Asthma is a chronic disease with no known cure. Substantial alleviation of asthma symptoms is possible via preventive therapy, such as the use of bronchodilators and anti-inflammatory agents. Asthma management is aimed at improving the quality of life of asthma patients.

Monitoring of lung function is viewed as a major factor in determining an appropriate treatment, as well as in patient follow-up. Preferred therapies are often based on aerosol-type medications to minimize systemic side-effects. The efficacy of aerosol type therapy is highly dependent on patient compliance, which is difficult to assess and maintain, further contributing to the importance of lung-function monitoring.

Asthma episodes usually develop over a period of several days, although they may sometimes seem to appear unexpectedly. The gradual onset of the asthmatic episode provides an opportunity to start countermeasures to stop and reverse the inflammatory process. Early treatment at the pre-episode stage may reduce the clinical episode manifestation considerably, and may even prevent the transition from the pre-clinical stage to a clinical episode altogether.

Two techniques are generally used for asthma monitoring. The first technique, spirometry, evaluates lung function using a spirometer, an instrument that measures the volume of air inhaled and exhaled by the lungs. Airflow dynamics are measured during a forceful, coordinated inhalation and exhalation effort by the patient into a mouthpiece connected via a tube to the spirometer. A peak-flow meter is a simpler device that is similar to the spirometer, and is used in a similar manner. The second technique evaluates lung function by measuring nitric-oxide concentration using a dedicated nitric-oxide monitor. The patient breathes into a mouthpiece connected via a tube to the monitor.

Efficient asthma management requires daily monitoring of respiratory function, which is generally impractical, particularly in non-clinical or home environments. Peak-flow meters and nitric-oxide monitors provide a general indication of the status of lung function. However, these monitoring devices do not possess predictive value, and are used as during-episode markers. In addition, peak-flow meters and nitric-oxide monitors require active participation of the patient, which is difficult to obtain from many children and substantially impossible to obtain from infants.

CHF is a condition in which the heart is weakened and unable to circulate blood to meet the body's needs. The subsequent buildup of fluids in the legs, kidneys, and lungs characterizes the condition as congestive. The weakening may be associated with either the left, right, or both sides of the heart, with different etiologies and treatments associated with each type. In most cases, it is the left side of the heart which fails, so that it is unable to efficiently pump blood to the systemic circulation. The ensuing fluid congestion of the lungs results in changes in respiration, including alterations in rate and/or pattern, accompanied by increased difficulty in breathing and tachypnea.

Quantification of such abnormal breathing provides a basis for assessing CHF progression. For example, Cheyne-Stokes Respiration (CSR) is a breathing pattern characterized by rhythmic oscillation of tidal volume with regularly recurring periods of alternating apnea and hyperpnea. While CSR may be observed in a number of different pathologies (e.g., encephalitis, cerebral circulatory disturbances, and lesions of the bulbar center of respiration), it has also been recognized as an independent risk factor for worsening heart failure and reduced survival in patients with CHF. In CHF, CSR is associated with frequent awakening that fragments sleep, and with concomitant sympathetic activation, both of which may worsen CHF. Other abnormal breathing patterns may involve periodic breathing, prolonged expiration or inspiration, or gradual changes in respiration rate usually leading to tachypnea.

SUMMARY OF EMBODIMENTS

For some applications of the present invention, a subject's respiration rate is monitored for a duration of time of greater than two hours. A parameter of the subject's respiration rate over the time duration, such as the median respiration rate, the mean respiration rate, the maximum respiration rate, and/or a pattern of the respiration rate is determined. The parameter is compared to the same parameter as determined on a previous day during a time period that overlaps with (e.g., is substantially the same as, or partially overlaps with) the time period based upon which the parameter of respiration was determined on the present day. For example, the parameter is compared to the same parameter as determined on a previous day for the same time duration and at the same period (e.g., the same time) of the day. For example, the mean respiration rate over a time duration of three hours, between the times of 8 pm and 11 pm on the present day, may be compared with the mean respiration rate over a time duration of three hours between the times of 8 pm and 11 pm on the previous day. In response thereto, the likelihood of the subject subsequently undergoing an adverse clinical event is determined. Typically, it is determined that the subject is likely to undergo an adverse clinical event by determining that the difference between the parameter of respiration (e.g., the mean respiration rate) of the present day and of the previous day is greater than a threshold amount, e.g., by determining that the parameter of respiration of the present day and that of the previous day are substantially different. Typically, in response to determining that the subject is likely to undergo an adverse clinical event, an alert is generated.

For some applications, the techniques described in the above paragraph with respect to the subject's respiration rate are applied with respect to the subject's heart rate and/or with respect to the subject's respiration rate and the subject's heart rate. For example, it may be determined that the subject is likely to undergo an adverse clinical event by determining that the difference between a parameter of the subject's cardiac cycle (e.g., the mean heart rate over a time duration of greater than two hours at a given period of the day) of the present day and of a previous day is greater than a threshold amount, e.g., by determining that the parameter of the cardiac cycle of the present day and that of the previous day are substantially different. Or, it may be determined that the subject is likely to undergo an adverse clinical event by determining that the difference between a parameter of the subject's cardiac cycle of the present day and of a previous day is greater than a threshold amount, and the difference between a parameter of the subject's respiration of the present day and of a previous day is greater than a threshold amount.

For some applications of the present invention, a subject's motion is monitored for a duration of time of greater than two hours. A parameter of the subject's motion, such as total duration that the subject is in motion, or percentage of time that the subject is in motion, over the time duration is determined. The parameter is compared to the same parameter as determined on a previous day during a time period that overlaps with (e.g., is substantially the same as, or partially overlaps with) the time period based upon which the parameter of respiration was determined on the present day. For example, the parameter is compared to the same parameter as determined on a previous day for the same time duration and at the same period (e.g., the same time) of the day. For example, the total time that the subject is in motion, or percentage of time that the subject is in motion over a time duration of three hours, between the times of 8 pm and 11 pm on the present day, may be compared with the total time that the subject is in motion, or percentage of time that the subject is in motion over a time duration of three hours between the times of 8 pm and 11 pm on the previous day. In response thereto, the likelihood of the subject subsequently undergoing an adverse clinical event is determined. Typically, it is determined that the subject is likely to undergo an adverse clinical event by determining that the difference between the parameter of motion of the present day and of the previous day is greater than a threshold amount, e.g., by determining that the parameter of motion of the present day and that of the previous day are substantially different. Typically, in response to determining that the subject is likely to undergo an adverse clinical event, an alert is generated.

For some applications, the threshold of the cardiac cycle (described hereinabove) is set responsively to a detected respiration rate, and/or responsively to a detected parameter of the subject's motion. Alternatively or additionally, the threshold of the parameter of the subject's respiration (described hereinabove) is set responsively to the detected heart rate, and/or responsively to a detected parameter of the subject's motion. Further alternatively or additionally, the threshold of the parameter of the subject's motion (described hereinabove) is set responsively to the detected heart rate, and/or responsively to the detected respiration rate.

There is therefor provided, in accordance with some applications of the present invention, apparatus, including:

a mechanical sensor configured to detect a physiological signal of a subject without contacting or viewing the subject or clothes that the subject is wearing;

a control unit configured to:
  receive the physiological signal from the sensor over a time duration of at least two hours at a given period of at least one first baseline day,
  determine a physiological parameter of the subject based upon the received physiological signal of the first baseline day;
  receive the physiological signal from the sensor over a time duration of at least two hours at a given period of a second day, the period over which the subject's physiological signal is detected on the second day overlapping with the period over which the subject's physiological signal is detected on the first baseline day;
  determine a physiological parameter of the subject based upon the received physiological signal of the second day;
  compare the physiological parameter based upon the received physiological signal of the second day to the baseline physiological parameter of the subject; and
  generate an alert in response to the comparison; and an output unit configured to output the alert.

For some applications, the physiological sensor is configured to detect the physiological signal of the subject by detecting a respiration rate of the subject.

For some applications, the physiological sensor is configured to detect the physiological signal of the subject by detecting a heart rate of the subject.

For some applications, the physiological sensor is configured to detect the physiological signal of the subject by detecting a parameter of motion of the subject.

There is further provided, in accordance with some applications of the present invention, apparatus, including:
a sensor configured to detect a respiration signal indicative of a respiration rate of a subject; and
a control unit configured to:
receive the detected respiration signal from the sensor over a time duration of at least two hours at a given period of at least one first respiration-rate baseline day;
determine a baseline parameter of the subject's respiration based upon the received respiration signal of the first respiration-rate baseline day;
receive the detected respiration signal from the sensor over a time duration of at least two hours at a given period of a second day, the period over which the subject's respiration is detected on the second day overlapping with the period over which the subject's respiration is detected on the first respiration-rate baseline day;
determine a parameter of the subject's respiration based upon the received respiration signal of the second day;
compare the parameter of the subject's respiration based upon the received respiration signal of the second day to the baseline parameter of the subject's respiration; and
generate an alert in response to the comparison; and an output unit configured to output the alert.

For some applications, the control unit is configured to determine the baseline parameter of respiration by determining a baseline respiration pattern based upon the received respiration signal of the first respiration-rate baseline day, and the control unit is configured to determine the parameter of the subject's respiration based upon the received respiration signal of the second day by determining a respiration pattern based upon the received respiration signal of the second day.

For some applications:
the control unit is configured to determine the baseline parameter of respiration by determining a parameter selected from the group consisting of: a mean respiration rate, a maximum respiration rate, and a median respiration rate, based upon the received respiration signal of the first respiration-rate baseline day, and
the control unit is configured to determine the parameter of the subject's respiration based upon the received respiration signal of the second day by determining a parameter selected from the group consisting of: a mean respiration rate, a maximum respiration rate, and a median respiration rate, based upon the received respiration signal of the second day.

For some applications, the control unit is configured to:
receive a heart-rate signal from the sensor indicative of a heart rate of the subject over a time duration of at least two hours at a given period of at least one first heart-rate baseline day;
determine a baseline parameter of the subject's cardiac cycle based upon the received heart-rate signal of the first heart-rate baseline day;
receive a heart-rate signal from the sensor indicative of a heart rate of the subject over a time duration of at least two hours at the given period of the second day, the period over which the subject's heart rate is detected on the second day overlapping with the period over which the subject's heart rate is detected on the first heart-rate baseline day;
determine a parameter of the subject's cardiac cycle based upon the received heart-rate signal of the second day; and
compare the parameter of the subject's cardiac cycle based upon the received heart-rate signal of the second day to the baseline parameter of the cardiac cycle, and
generate the alert by generating the alert in response to (a) the comparison of the parameter of the subject's respiration based upon the received respiration signal of the second day to the baseline parameter of the subject's respiration, and (b) the comparison of the parameter of the subject's cardiac cycle based upon the received heart-rate signal of the second day to the baseline parameter of the subject's cardiac cycle.

For some applications, the control unit is configured to:
receive a motion signal from the sensor indicative of motion of the subject over a time duration of at least two hours at a given period of at least one first motion-parameter baseline day;
determine a baseline parameter of the subject's motion based upon the received motion signal of the first motion-parameter baseline day;
receive a motion signal from the sensor indicative of motion of the subject over a time duration of at least two hours at the given period of the second day, the period over which the subject's motion is detected on the second day overlapping with the period over which the subject's motion is detected on the first motion-parameter baseline day;
determine a parameter of the subject's motion based upon the received motion signal of the second day; and
compare the parameter of the subject's motion based upon the received motion signal of the second day to the baseline parameter of motion, and
generate the alert by generating the alert in response to (a) the comparison of the parameter of the subject's respiration based upon the received respiration signal of the second day to the baseline parameter of the subject's respiration, and (b) the comparison of the parameter of the subject's motion based upon the received motion signal of the second day to the baseline parameter of the subject's motion.

For some applications, the control unit is configured to compare the parameter of the subject's respiration based upon the received respiration signal of the second day to the baseline parameter of the subject's respiration by determining whether the parameter of the subject's respiration based upon the received respiration signal of the second day differs from the baseline parameter of the subject's respiration by more than a threshold amount.

For some applications, the control unit is configured to:
receive a heart-rate signal from the sensor indicative of a heart rate of the subject; and
set the threshold in response to the detected heart-rate signal.

For some applications, the control unit is configured to:
receive a motion signal from the sensor indicative of a motion of the subject; and
set the threshold in response to the detected motion signal.

There is additionally provided, in accordance with some applications of the present invention, apparatus, including:
a sensor configured to detect a heart-rate signal indicative of a heart rate of a subject; and
a control unit configured to:
receive the detected heart-rate signal from the sensor over a time duration of at least two hours at a given period of at least one first heart-rate baseline day;
determine a baseline parameter of the subject's cardiac cycle based upon the received heart-rate signal of the first heart-rate baseline day;
receive the detected heart-rate signal from the sensor over a time duration of at least two hours at a given period of a second day, the period over which the subject's heart rate is detected on the second day overlapping with the period over which the subject's heart rate is detected on the first heart-rate baseline day;
determine a parameter of the subject's cardiac cycle based upon the received heart-rate signal of the second day;

compare the parameter of the subject's cardiac cycle based upon the received heart-rate signal of the second day to the baseline parameter of the subject's cardiac cycle; and generate an alert in response to the comparison; and an output unit configured to output the alert.

For some applications, the control unit is configured to:

receive a motion signal from the sensor indicative of motion of the subject over a time duration of at least two hours at a given period of at least one first motion-parameter baseline day;

determine a baseline parameter of the subject's motion based upon the received motion signal of the first motion-parameter baseline day;

receive a motion signal from the sensor indicative of motion of the subject over a time duration of at least two hours at the given period of the second day, the period over which the subject's motion is detected on the second day overlapping with the period over which the subject's motion is detected on the first motion-parameter baseline day;

determine a parameter of the subject's motion based upon the received motion signal of the second day; and compare the parameter of the subject's motion based upon the received motion signal of the second day to the baseline parameter of motion, and generate the alert by generating the alert in response to (a) the comparison of the parameter of the subject's cardiac cycle based upon the received heart-rate signal of the second day to the baseline parameter of the subject's cardiac cycle, and (b) the comparison of the parameter of the subject's motion based upon the received motion signal of the second day to the baseline parameter of the subject's motion.

For some applications, the control unit is configured to compare the parameter of the subject's cardiac cycle based upon the received heart-rate signal of the second day to the baseline parameter of the subject's cardiac cycle by determining whether the parameter of the subject's cardiac cycle based upon the received heart-rate signal of the second day differs from the baseline parameter of the subject's cardiac cycle by more than a threshold amount.

For some applications, the control unit is configured to:

receive a respiration signal from the sensor indicative of a respiration rate of the subject; and set the threshold in response to the detected respiration signal.

For some applications, the control unit is configured to:

receive a motion signal from the sensor indicative of a motion of the subject; and set the threshold in response to the detected motion signal.

There is further provided, in accordance with some applications of the present invention, apparatus, including:

a sensor configured to detect a motion signal indicative of motion of a subject; and a control unit configured to:

receive the detected motion signal from the sensor over a time duration of at least two hours at a given period of at least one first motion-parameter baseline day;

determine a baseline parameter of the subject's motion based upon the received motion signal of the first motion-parameter baseline day;

receive the detected motion signal from the sensor over a time duration of at least two hours at a given period of a second day, the period over which the subject's motion is detected on the second day overlapping with the period over which the subject's motion is detected on the first motion-parameter baseline day;

determine a parameter of the subject's motion based upon the received motion signal of the second day;

compare the parameter of the subject's motion based upon the received motion signal of the second day to the baseline parameter of the subject's motion; and generate an alert in response to the comparison; and an output unit configured to output the alert.

For some applications, the control unit is configured to compare the parameter of the subject's motion based upon the received motion signal of the second day to the baseline parameter of the subject's motion by determining whether the parameter of the subject's motion based upon the received motion signal of the second day differs from the baseline parameter of the subject's motion by more than a threshold amount.

For some applications, the control unit is configured to:

receive a respiration signal from the sensor indicative of a respiration rate of the subject; and set the threshold in response to the detected respiration signal.

For some applications, the control unit is configured to:

receive a heart-rate signal from the sensor indicative of a heart rate of the subject; and set the threshold in response to the detected heart-rate signal.

There is additionally provided, in accordance with some applications of the present invention, a method including:

detecting a respiration rate of a subject over a time duration of at least two hours at a given period of at least one first respiration-rate baseline day;

determining a baseline parameter of the subject's respiration based upon the detected respiration rate for the first respiration-rate baseline day;

detecting a respiration rate of the subject over a time duration of at least two hours at a given period of a second day, the period over which the subject's respiration is detected on the second day overlapping with the period over which the subject's respiration is detected on the first respiration-rate baseline day;

determining a parameter of the subject's respiration based upon the detected respiration rate on the second day;

comparing the parameter of the subject's respiration based upon the detected respiration rate on the second day to the baseline parameter of the subject's respiration; and generating an alert in response to the comparison.

There is further provided, in accordance with some applications of the present invention, a method including:

detecting a heart rate of a subject over a time duration of at least two hours at a given period of at least one first heart-rate baseline day;

determining a baseline parameter of the subject's cardiac cycle based upon the detected heart rate for the first heart-rate baseline day;

detecting a heart rate of the subject over a time duration of at least two hours at a given period of a second day, the period over which the subject's heart rate is detected on the second day overlapping with the period over which the subject's heart rate is detected on the first heart-rate baseline day;

determining a parameter of the subject's cardiac cycle based upon the detected heart rate on the second day;

comparing the parameter of the subject's cardiac cycle based upon the detected heart rate on the second day to the baseline parameter of the subject's cardiac cycle; and generating an alert in response to the comparison.

There is additionally provided, in accordance with some applications of the present invention, a method including:

detecting motion of a subject over a time duration of at least two hours at a given period of at least one first motion-parameter baseline day;

determining a motion parameter of the subject's respiration based upon the detected motion for the first motion-parameter baseline day;

detecting motion of the subject over a time duration of at least two hours at a given period of a second day, the period over which the subject's motion is detected on the second day overlapping with the period over which the subject's motion is detected on the first motion-parameter baseline day;

determining a parameter of the subject's motion based upon the motion detected on the second day;

comparing the parameter of the subject's motion based upon the motion detected on the second day to the baseline parameter of the subject's motion; and generating an alert in response to the comparison.

There is further provided, in accordance with some applications of the present invention, a method including:

detecting a physiological signal of a subject over a time duration of at least two hours at a given period of at least one first baseline day, without contacting or viewing the subject or clothes that the subject is wearing;

determining a physiological parameter of the subject based upon the detected physiological signal for the first baseline day;

detecting the physiological signal of the subject over a time duration of at least two hours at a given period of a second day, the period over which the subject's physiological signal is detected on the second day overlapping with the period over which the physiological signal is detected on the first baseline day;

determining a physiological parameter of the subject based upon the detected physiological signal on the second day;

comparing the physiological parameter based upon the detected physiological signal on the second day to the baseline physiological parameter of the subject; and generating an alert in response to the comparison.

In some embodiments, the present invention includes methods and systems for monitoring or predicting apnea events, for example, during sleep. These methods and systems may include use of a motion acquisition module, a pattern analysis module, and an output module. In one aspect, the methods and systems may be used for monitoring a patient's clinical parameters during sleep and identifying and predicting the onset of apnea events, and activating immediate treatment.

Another embodiment of the invention is a method of detecting an onset of apnea, the method comprising sensing motion of a subject, for example, without contacting the subject, the motion comprising motions related to at least breathing, and generating a signal corresponding to the sensed motion; extracting a breathing-related signal from the sensed motion signal corresponding to the breathing of the subject; and analyzing the breathing-related signal to predict the onset of apnea. In one aspect, the method may also comprise extracting and analyzing a heart rate signal. In one aspect, analyzing comprises detecting an increase in amplitude of at least one of the breathing-related signal and the heartbeat-related signal to detect the onset of apnea.

Another embodiment of the invention is a system for detecting an onset of apnea, the system comprising at least one sensor adapted to sense motion of a subject, for example, without contacting the subject, the motion comprising motions related to at least breathing, and generate a signal corresponding to the sensed motion; and an analyzer adapted to extract a breathing-related signal from the sensed motion signal corresponding to the breathing of the subject, and analyze the breathing-related signal to predict the onset of apnea. In one aspect, the analyzer may also extract a heartbeat signal from the sensed motion signal and analyze the heartbeat signal to predict the onset of apnea.

Another embodiment of the invention is a method of detecting the onset of apnea, the method comprising sensing an audio signal, for example, near the subject; sensing breathing of the subject, for example, without contacting the subject, and generating a breathing-related signal corresponding to the sensed breathing; analyzing the audio signal and the breathing-related signal to detect the onset of apnea.

Another embodiment of the invention is an apparatus for detecting the onset of apnea, the apparatus comprising an audio sensor adapted to generate an audio signal; at least one sensor adapted to sense breathing of the subject, for example, without contacting the subject, and generate a breathing-related signal corresponding to the sensed breathing; and an analyzer adapted to analyze the audio signal and the breathing-related signal to detect the onset of apnea.

There is therefore provided, in accordance with some applications of the present invention, a method for predicting an onset of apnea, the method including:

sensing motion of a subject without contacting the subject, the motion including motions related to at least breathing, and generating a signal corresponding to the sensed motion;

extracting a breathing-related signal from the sensed motion signal; and predicting the onset of apnea at least partially in response to analyzing the breathing-related signal.

For some applications, the motion further includes motions related to heartbeat, the method further includes extracting a heartbeat-related signal from the sensed motion signal, and predicting the onset of apnea is at least partially in response to analyzing the heartbeat-related signal.

For some applications, the method is practiced without requiring compliance of the subject.

For some applications, the method further includes treating the subject for apnea when the onset of apnea is predicted.

There is further provided, in accordance with some applications of the present invention, a system for predicting an onset of apnea, the system including:

at least one sensor adapted to
sense motion of a subject without contacting the subject, the sensed motion including motions related to at least breathing, and
generate a signal corresponding to the sensed motion; and
an analyzer adapted to
extract a breathing-related signal from the sensed motion signal, and
analyze the breathing-related signal to predict the onset of apnea.

For some applications, the sensed motion further includes motions related to heartbeat, and the analyzer is further adapted to:

extract a heartbeat-related signal from the sensed motion signal, and analyze the heartbeat-related signal to predict the onset of apnea.

For some applications, the system further includes an apnea treatment device that is activated when the onset of apnea is predicted.

There is further provided, in accordance with some applications of the present invention, a method of detecting an onset of apnea, the method including:

sensing an audio signal near a subject;

sensing breathing of the subject without contacting the subject and generating a breathing-related signal corresponding to the sensed breathing; and analyzing the audio signal and the breathing-related signal to detect the onset of apnea.

For some applications, the analyzing includes detecting a decrease in amplitude of the audio signal and correlating the decrease with little or no decrease in amplitude of the breathing-related signal.

For some applications, the method is practiced during periods of snoring.

For some applications, the method further includes, following detection of the onset of apnea, activating a therapeutic device to at least reduce the apnea.

For some applications, the method further includes deactivating the therapeutic device when the apnea subsides.

For some applications, the method is practiced without contacting or viewing clothes the subject is wearing.

For some applications, the method is practiced without requiring compliance of the subject.

There is further provided, in accordance with some applications of the present invention, apparatus for detecting an onset of apnea, the apparatus including:

an audio sensor adapted to sense noise from a subject and generate an audio signal corresponding to the sensed noise;

at least one sensor adapted to sense breathing of the subject without contacting the subject and generate a breathing-related signal corresponding to the sensed breathing; and an analyzer adapted to analyze the audio signal and the breathing-related signal to detect the onset of apnea.

For some applications, the analyzer is adapted to detect a decrease in amplitude of the audio signal and correlate the decrease with little or no decrease in amplitude of the breathing-related signal.

For some applications, the audio sensor is adapted to detect snoring.

For some applications, the apparatus further includes a therapeutic device and means for activating the therapeutic device when the onset of apnea is detected.

For some applications, the apparatus further includes means for deactivating the therapeutic device when the apnea subsides.

The present invention will be more fully understood from the following detailed description of embodiments thereof, taken together with the drawings, in which:

BRIEF DESCRIPTION OF THE DRAWINGS

FIG. 2 is a schematic block diagram illustrating components of a control unit of the system of FIG. 1, in accordance with some applications of the present invention;

FIGS. 3A-D are graphs showing the results of experiments conducted, in accordance with some applications of the present invention;

FIG. 4 is a graph illustrating breathing rate patterns of a chronic asthma patient, which is the same as FIG. 4 of U.S. Pat. No. 7,077,810 to Lange, which is incorporated herein by reference;

FIGS. 5 and 6 are graphs of exemplary baseline and measured breathing rate and heart rate nighttime patterns, respectively, which are generally similar to FIGS. 6 and 7 of U.S. Pat. No. 7,314,451 to Halperin, which is incorporated herein by reference.

DETAILED DESCRIPTION OF EMBODIMENTS

Figure 1:
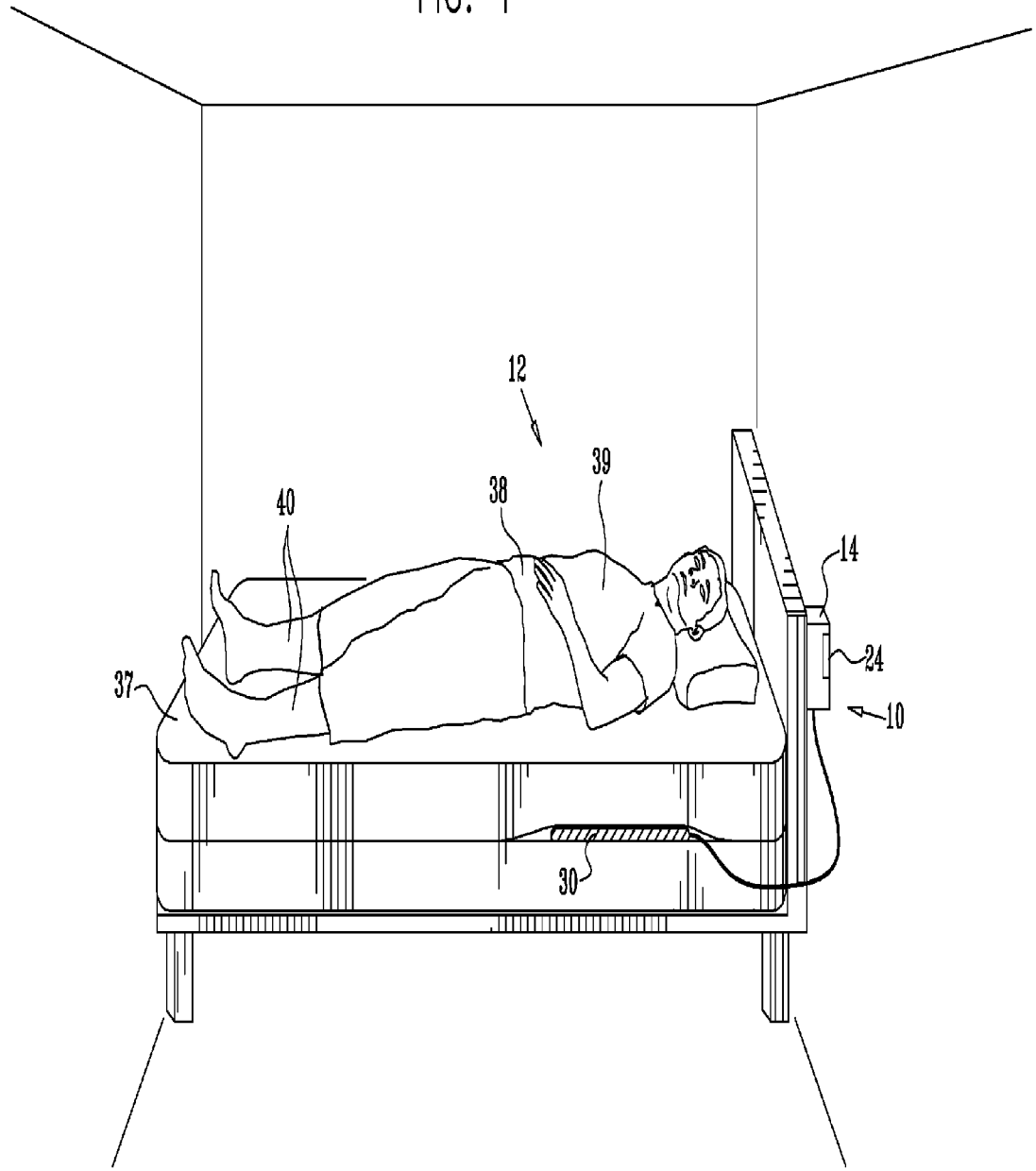
FIG. 1 is a schematic illustration of a system for monitoring a chronic medical condition of a subject, in accordance with some applications of the present invention.

Reference is made to FIG. 1, which is a schematic illustration of a system 10 for monitoring a chronic medical condition of a subject 12, in accordance with some applications of the present invention. System 10 typically comprises a mechanical sensor 30 (e.g., a motion sensor), a control unit 14, and a user interface 24. For some applications, user interface 24 is integrated into control unit 14, as shown in the figure, while for other applications, the user interface and control unit are separate units. For some applications, motion sensor is integrated into control unit 14, in which case user interface 24 is either also integrated into control unit 14 or remote from control unit 14.

FIG. 2 is a schematic block diagram illustrating components of control unit 14, in accordance with some applications of the present invention. Control unit 14 typically comprises a motion data acquisition module 20 and a pattern analysis module 16. Pattern analysis module 16 typically comprises one or more of the following modules: a breathing pattern analysis module 22, a heartbeat pattern analysis module 23, a cough analysis module 26, a restlessness analysis module 28, a blood pressure analysis module 29, and an arousal analysis module 31. For some applications, two or more of analysis modules 20, 22, 23, 26, 28, 29, and 31 are packaged in a single housing. For other applications, the modules are packaged separately (for example, so as to enable remote analysis by one or more of the pattern analysis modules of breathing signals acquired locally by data acquisition module 20). For some applications, user interface comprises a dedicated display unit such as an LCD or CRT monitor. Alternatively or additionally, user interface 24 includes a communication line for relaying the raw and/or processed data to a remote site for further analysis and/or interpretation.

For some applications of the present invention, data acquisition module 20 is adapted to non-invasively monitor breathing and heartbeat patterns of subject 12. Breathing pattern analysis module 22 and heartbeat pattern analysis module are adapted to analyze the respective patterns in order to (a) predict an approaching clinical event, such as an asthma attack or heart condition-related lung fluid buildup, and/or (b) monitor the severity and progression of a clinical event as it occurs. For some applications, breathing pattern analysis module 22 and heartbeat pattern analysis module 23 are adapted to analyze the respective patterns in order to determine a likelihood of an approaching adverse clinical event without necessarily identifying the nature of the event. User interface 24 is adapted to notify subject 12 and/or a healthcare worker of the predicted or occurring event. Prediction of an approaching clinical event facilitates early preventive treatment, which generally reduces the required dosage of medication, and/or lowers mortality and morbidity. When treating asthma, such a reduced dosage generally minimizes the side-effects associated with high dosages typically required to reverse the inflammatory condition once the event has begun.

For some applications of the present invention, pattern analysis module 16 combines parameter data generated from two or more of analysis modules 20, 22, 23, 26, 28, 29, and analyzes the combined data in order to predict and/or monitor a clinical event. For some applications, pattern analysis module 16 derives a score for each parameter based on the parameter's deviation from baseline values (either for the specific patient or based on population averages). Pattern analysis module 16 combines the scores, such as by taking an average, maximum, standard deviation, or other function of the scores. The combined score is compared to one or more threshold values (which may be predetermined) to determine whether an event is predicted, currently occurring, or neither predicted nor occurring, and/or to monitor the severity and progression of an occurring event. For some applications, pattern analysis module 16 learns the criteria and/or functions for combining the individual parameter scores for the specific patient or patient group based on personal history. For example, pattern analysis module 16 may perform such learning by analyzing parameters measured prior to previous clinical events.

Although system 10 may monitor breathing and heartbeat patterns at any time, for some conditions it is generally most effective to monitor such patterns during sleep at night. When the subject is awake, physical and mental activities unrelated to the monitored condition often affect breathing and heartbeat patterns. Such unrelated activities generally have less influence during most night sleep. For some applications, system 10 monitors and records patterns throughout all or a large portion of a night. The resulting data set generally encompasses typical long-term respiratory and heartbeat patterns, and facilitates comprehensive analysis. Additionally, such a large data set enables rejection of segments contaminated with movement or other artifacts, while retaining sufficient data for a statistically significant analysis.

Reference is again made to FIG. 2. Data acquisition module typically comprises circuitry for processing the raw motion signal generated by motion sensor 30, such as at least one pre-amplifier 32, at least one filter 34, and an analog-to-digital (A/D) converter 36. Filter 34 typically comprises a band-pass filter or a low-pass filter, serving as an anti-aliasing filter with a cut-off frequency of less than one half of the sampling rate. The low-passed data is typically digitized at a sampling rate of at least 10 Hz and stored in memory. For example, the anti-aliasing filter cut-off may be set to 5 Hz and the sampling rate set to 40 Hz.

Reference is again made to FIG. 1. Typically, motion sensor 30 detects one or more physiological signal of the subject without contacting or viewing the subject or clothes that the subject is wearing. For some applications of the present invention, motion sensor 30 comprises a pressure gauge (e.g., a piezoelectric sensor) or a strain gauge (e.g., a silicon or other semiconductor strain gauge, or a metallic strain gauge), which is typically adapted to be installed in, on, or under a reclining surface 37 upon which the subject lies, e.g., sleeps, and to sense breathing- and heartbeat-related motion of the subject. "Pressure gauge," as used in the claims, includes, but is not limited to, all of the gauges mentioned in the previous sentence. Typically, reclining surface 37 comprises a mattress, a mattress covering, a sheet, a mattress pad, and/or a mattress cover. For some applications, motion sensor 30 is integrated into reclining surface 37, e.g., into a mattress, and the motion sensor and reclining surface are provided together as an integrated unit. For some applications, motion sensor 30 is adapted to be installed in, on, or under reclining surface 37 in a vicinity of an abdomen 38 or chest 39 of subject 12.

Alternatively or additionally, motion sensor 30 is installed in, on, or under reclining surface 37 in a vicinity of a portion of subject 12 anatomically below a waist of the subject, such as in a vicinity of legs 40 of the subject. For some applications, such positioning provides a clearer pulse signal than positioning the sensor in a vicinity of abdomen 38 or chest 39 of the subject. For some applications, motion sensor 30 comprises a fiber optic sensor, for example, as described by Butter and Hocker in Applied Optics 17: 2867-2869 (Sep. 15, 1978).

For some applications, the pressure or strain gauge is encapsulated in a rigid compartment, which typically has a surface area of at least 10 cm$^2$, and a thickness of less than 5 mm. The gauge output is channeled to an electronic amplifier, such as a charge amplifier typically used with piezoelectric accelerometers and capacitive transducers to condition the extremely high output impedance of the transducer to a low impedance voltage suitable for transmission over long cables. The strain gauge and electronic amplifier translate the mechanical vibrations into electrical signals. Alternatively, the strain gauge output is amplified using a Wheatstone bridge and an amplifier such as Analog Device Module Numbers 3B16, for a minimal bandwidth, or 3B18, for a wider bandwidth (National Instruments Corporation, Austin, Tex., USA).

For some applications of the present invention, motion sensor 30 comprises a grid of multiple pressure or strain gauge sensors, adapted to be installed in, on, or under reclining surface 37. The use of such a grid, rather than a single gauge, may improve breathing and heartbeat signal reception.

Breathing pattern analysis module 22 is adapted to extract breathing patterns from the motion data, and heartbeat pattern analysis module 23 is adapted to extract heartbeat patterns from the motion data. Alternatively or additionally, system 10 comprises another type of sensor, such as an acoustic or air-flow sensor, attached or directed at the subject's face, neck, chest and/or back.

For some applications of the present invention, the subject's respiration rate is monitored for a duration of time of greater than two hours (e.g., greater than three hours, greater than four hours, greater than five hours, or greater than six hours). Breathing pattern analysis module 22 determines a parameter of the subject's respiration rate over the time duration, such as the median respiration rate, the mean respiration rate, the maximum respiration rate, and/or a respiration rate pattern. Module 22 compares the determined parameter to the same parameter as determined on a previous day during a time period that overlaps with the time period based upon which the parameter of respiration was determined on the present day. For example, the parameter is compared to the same parameter as determined on a previous day for the same time duration and at the same period (e.g., the same time) of the day.

For example, the mean respiration rate over a time duration of three hours, between the times of 8 pm and 11 pm on the present day, may be compared with the mean respiration rate over a time duration of three hours between the times of 8 pm and 11 pm on the previous day. In response thereto, the likelihood of the subject subsequently undergoing an adverse clinical event is determined. Typically, it is determined that the subject is likely to undergo an adverse clinical event by determining that the difference between the parameter of respiration (e.g., the mean respiration rate) of the present day and of the previous day is greater than a threshold amount. Typically, in response to determining that the subject is likely to undergo an adverse clinical event, an alert is generated by user interface 24.

For some applications, the period of to the day which is compared to the same period of the previous day is a time period, e.g., between 8 pm and 11 pm, as described hereinabove. Alternatively, the period may be defined with respect to the subject's circadian clock, e.g., the period may be the first three hours of the subject's sleep, or from the beginning of the second hour of the subject's sleep to the end of the fifth hour of the subject's sleep.

For some applications, heartbeat pattern analysis module 23 applies generally similar analysis to the subject's heart rate to that described hereinabove with respect to the breathing pattern analysis module 22. For example, module 23 may determine that the subject is likely to undergo an adverse clinical event by determining that the difference between a parameter of the subject's cardiac cycle (e.g., the mean heart rate over a time duration of greater than two hours at a given period of the day) on the present day and that of a previous day is greater than a threshold amount. For some applications, control unit 24 determines that the subject is likely to undergo an adverse clinical event by determining that the difference between a parameter of the subject's cardiac cycle on the present day and that of a previous day is greater than a threshold amount, and the difference between a parameter of the subject's respiration on the present day and that of the previous day is greater than a threshold amount.

As described hereinabove, for some applications, breathing pattern analysis module 22 and heartbeat pattern analysis module 23 are adapted to analyze the respective patterns in order to determine a likelihood of an approaching adverse clinical event without necessarily identifying the nature of the event. Thus, for some applications, in response to determining that the subject is likely to undergo an adverse clinical event, the user interface generates a generic alert signal, in order to indicate to a healthcare professional that an adverse clinical event is imminent.

For some applications, system 10 applies generally similar analysis to a different physiological parameter of the subject to that described hereinabove with respect to the breathing pattern analysis module 22. For example, the system may apply the analysis to a parameter of the subject's motion, such as the total time that the subject is in motion, or percentage of time that the subject is in motion over a given time duration.

Reference is now made to FIGS. 3A-D, which are graphs showing the results of experiments conducted, in accordance with some applications of the present invention. Earlysense Ltd. (Israel) manufactures the EverOn™ system, which is a contact-less piezoelectric sensor placed under a subject's mattress that provides continuous measurement of heart rate and respiration rate of the subject, generally in accordance with the techniques described hereinabove.

A non-interventional study was conducted in two internal medicine departments (Sheba Medical Center and Meir Medical Center, both in Israel). Patients who were admitted due to an acute respiratory condition were enrolled on the study. Patients were monitored by the EverOn™ sensor and followed for major clinical episodes. A major clinical event was defined as death, transfer to ICU, or intubation and mechanical ventilation on the floors. Out of 149 patients included in the study, 96 patients had a length of stay that allowed at least one comparable time window. Ten major clinical events were recorded for these patients. Retrospective analysis of continuous respiratory and heart signal recording was performed. The median respiration rate and heart rate over 6-hour time durations (00-06, 06-12, 12-18, and 18-24) were compared to the median respiration rate and heart rate over a corresponding 6-hour time duration on the previous day. Similarly, the maximum respiration rate and heart rate over 6-hour time durations (00-06, 06-12, 12-18, and 18-24) were compared to the maximum respiration rate and heart rate over a corresponding 6-hour time duration on the previous day. Retrospective receiver operating characteristic (ROC) curve analysis was applied to the results to determine the sensitivity, specificity, positive predictive value, and negative predictive value of using respective thresholds (i.e., thresholds for the difference between median or maximum respiration rate or heart rate and those of the previous day) for determining the likelihood of a subject undergoing (a) any adverse clinical event, i.e., either a major or a moderate clinical event (such as a non-major respiratory event requiring immediate intervention, e.g., bilevel positive airway pressure (BIPAP) or continuous positive airway pressure (CPAP)), or (b) a major clinical event.

Table 1 (shown below) shows the results of the ROC curve analysis of respective combinations of median heart rate and respiration rate thresholds (i.e., thresholds for the difference between median heart rate and respiration rate and those of the previous day) with respect to determining the likelihood of a subject undergoing any adverse clinical event, i.e., either a major or a moderate clinical event.

TABLE 1

| Threshold Heart rate (beats per minute) - Respiration rate (breaths per minute)) | Sensitivity | Specificity | PPV | NPV |
| --- | --- | --- | --- | --- |
| 14-3 | 67 | 82 | 35 | 95 |
| 14-4 | 67 | 82 | 35 | 95 |
| 14-5 | 67 | 86 | 40 | 95 |
| 14-6 | 58 | 89 | 44 | 94 |
| 16-3 | 67 | 87 | 42 | 95 |
| 16-4 | 67 | 87 | 42 | 95 |
| 16-5 | 67 | 89 | 47 | 95 |
| 16-6 | 58 | 93 | 54 | 94 |
| 18-3 | 67 | 89 | 47 | 95 |
| 18-4 | 67 | 89 | 47 | 95 |
| 18-5 | 67 | 90 | 50 | 95 |
| 18-6 | 58 | 94 | 58 | 94 |
| 20-3 | 67 | 94 | 62 | 95 |
| 20-4 | 67 | 94 | 62 | 95 |
| 20-5 | 67 | 95 | 67 | 95 |
| 20-6 | 58 | 98 | 78 | 94 |
| 22-3 | 67 | 94 | 62 | 95 |
| 22-4 | 67 | 94 | 62 | 95 |
| 22-5 | 67 | 95 | 67 | 95 |
| 22-6 | 58 | 98 | 78 | 94 |

Table 2 (shown below) shows the results of the ROC curve analysis of respective combinations of median heart rate and respiration rate (i.e., thresholds for the difference between median heart rate and respiration rate and those of the previous day) thresholds with respect to determining the likelihood of a subject undergoing a major clinical event.

TABLE 2

| Threshold (Heart rate (beats per minute) - Respiration rate (breaths per minute)) | Sensitivity | Specificity | PPV | NPV |
| --- | --- | --- | --- | --- |
| -3 | 80 | 83 | 35 | 97 |
| 14-4 | 80 | 83 | 35 | 97 |
| 14-5 | 80 | 86 | 40 | 97 |
| 14-6 | 70 | 90 | 44 | 96 |
| 16-3 | 80 | 87 | 42 | 97 |
| 16-4 | 80 | 87 | 42 | 97 |
| 16-5 | 80 | 90 | 47 | 97 |
| 16-6 | 70 | 93 | 54 | 96 |

TABLE 2-continued

| Threshold (Heart rate (beats per minute) - Respiration rate (breaths per minute)) | Sensitivity | Specificity | PPV | NPV |
|---|---|---|---|---|
| 18-3 | 80 | 90 | 47 | 97 |
| 18-4 | 80 | 90 | 47 | 97 |
| 18-5 | 80 | 91 | 50 | 98 |
| 18-6 | 70 | 94 | 58 | 96 |
| 20-3 | 80 | 94 | 62 | 98 |
| 20-4 | 80 | 94 | 62 | 98 |
| 20-5 | 80 | 95 | 67 | 98 |
| 20-6 | 70 | 98 | 78 | 97 |
| 22-3 | 80 | 94 | 62 | 98 |
| 22-4 | 80 | 94 | 62 | 98 |
| 22-5 | 80 | 95 | 67 | 98 |
| 22-6 | 70 | 98 | 78 | 97 |

It is noted with respect to Tables 1 and 2 that the greatest sum of sensitivity and specificity is for thresholds of 20 or 22 for median heart rate in combination with a threshold of 5 for median respiration rate, both for predicting all adverse clinical events (i.e., major and minor adverse clinical events), and for predicting major clinical events.

Thus, for some applications of the present invention, a subject's heart rate and respiration rate are monitored. The median (or mean, or maximum) heart rate and respiration rate over a time duration of more than two hours and less than eight hours (e.g., greater than three hours, greater than four hours, greater than five hours, or greater than six hours) is determined and is compared to the median (or mean, or maximum) heart rate and respiration rate over a similar time duration at a similar period of the day (e.g., at the same time of day) on at least one previous day (e.g., the previous day). In response to determining (a) that the median (or mean, or maximum) heart rate on the present day differs from that of the previous day by a threshold amount of more than 15 beats per minute, e.g., more than 18 beats per minute, and (b) that the median (or mean, or maximum) respiration rate of the present day differs from that of the previous day by a threshold amount of more than 3 breaths per minute, e.g., more than 4 breaths per minute, then an alert is generated in order to indicate that an adverse clinical event is likely to occur.

Table 3 (shown below) shows the results of the ROC curve analysis of respective maximum heart rate thresholds (i.e., thresholds for the difference between the maximum heart rate and that of the previous day) with respect to determining the likelihood of a subject undergoing a major or a moderate clinical event.

TABLE 3

| Heart rate threshold (beats per minute) | Sensitivity | Specificity | Sum of Sensitivity and Specificity |
|---|---|---|---|
| 0.00 | 1.00 | 0.00 | 1.00 |
| 0.25 | 1.00 | 0.01 | 1.01 |
| 1.00 | 1.00 | 0.02 | 1.02 |
| 3.00 | 0.92 | 0.07 | 0.99 |
| 4.00 | 0.83 | 0.11 | 0.94 |
| 4.50 | 0.83 | 0.17 | 1.00 |
| 5.00 | 0.83 | 0.19 | 1.02 |
| 6.00 | 0.75 | 0.25 | 1.00 |
| 7.00 | 0.75 | 0.32 | 1.07 |
| 8.00 | 0.75 | 0.38 | 1.13 |
| 8.50 | 0.67 | 0.46 | 1.13 |
| 9.00 | 0.67 | 0.48 | 1.14 |
| 10.00 | 0.67 | 0.54 | 1.20 |
| 11.00 | 0.67 | 0.62 | 1.29 |
| 11.50 | 0.67 | 0.70 | 1.37 |
| 12.00 | 0.67 | 0.71 | 1.38 |
| 13.00 | 0.67 | 0.75 | 1.42 |
| 13.50 | 0.67 | 0.79 | 1.45 |
| 14.00 | 0.67 | 0.80 | 1.46 |
| 15.00 | 0.67 | 0.82 | 1.49 |
| 16.00 | 0.67 | 0.85 | 1.51 |
| 17.00 | 0.67 | 0.86 | 1.52 |
| 18.00 | 0.67 | 0.87 | 1.54 |
| 19.00 | 0.67 | 0.89 | 1.56 |
| 20.00 | 0.67 | 0.90 | 1.57 |
| 21.00 | 0.67 | 0.92 | 1.58 |
| 22.00 | 0.67 | 0.93 | 1.60 |
| 22.75 | 0.58 | 0.93 | 1.51 |
| 25.00 | 0.58 | 0.94 | 1.52 |
| 27.00 | 0.50 | 0.95 | 1.45 |
| 28.00 | 0.42 | 0.95 | 1.37 |
| 29.00 | 0.33 | 0.95 | 1.29 |
| 30.75 | 0.17 | 0.95 | 1.12 |
| 32.00 | 0.08 | 0.95 | 1.04 |
| 33.00 | 0.08 | 0.96 | 1.05 |
| 34.00 | 0.08 | 0.98 | 1.06 |
| 53.00 | 0.00 | 0.98 | 0.98 |
| 56.00 | 0.00 | 0.99 | 0.99 |

It is noted with respect to Table 3 that the greatest sum of sensitivity and specificity is for a heart rate threshold of 22 beats per minute, for predicting major and moderate adverse clinical events. FIG. 3A shows the ROC curve for a heart rate threshold of 22 with respect to predicting a likelihood of either a major or a moderate adverse clinical event. The area under the curve is 0.70 with a standard deviation of 0.11 and a p-value of 0.026.

Table 4 (shown below) shows the results of the ROC curve analysis of respective maximum heart rate thresholds (i.e., thresholds for the difference between the maximum heart rate and that of the previous day) with respect to determining the likelihood of a subject undergoing a major clinical event.

TABLE 4

| Heart rate threshold (beats per minute) | Sensitivity | Specificity | Sum of Sensitivity and Specificity |
|---|---|---|---|
| 0.00 | 1.00 | 0.00 | 1.00 |
| 0.25 | 1.00 | 0.01 | 1.01 |
| 1.00 | 1.00 | 0.02 | 1.02 |
| 3.00 | 1.00 | 0.08 | 1.08 |
| 4.00 | 0.90 | 0.12 | 1.02 |
| 4.50 | 0.90 | 0.17 | 1.07 |
| 5.00 | 0.90 | 0.20 | 1.10 |
| 6.00 | 0.80 | 0.26 | 1.06 |
| 7.00 | 0.80 | 0.33 | 1.13 |
| 8.00 | 0.80 | 0.38 | 1.18 |
| 8.50 | 0.80 | 0.48 | 1.28 |
| 9.00 | 0.80 | 0.49 | 1.29 |
| 10.00 | 0.80 | 0.55 | 1.35 |
| 11.00 | 0.80 | 0.63 | 1.43 |
| 11.50 | 0.80 | 0.71 | 1.51 |
| 12.00 | 0.80 | 0.72 | 1.52 |
| 13.00 | 0.80 | 0.76 | 1.56 |
| 13.50 | 0.80 | 0.79 | 1.59 |
| 14.00 | 0.80 | 0.80 | 1.60 |
| 15.00 | 0.80 | 0.83 | 1.63 |
| 16.00 | 0.80 | 0.85 | 1.65 |
| 17.00 | 0.80 | 0.86 | 1.66 |
| 18.00 | 0.80 | 0.87 | 1.67 |
| 19.00 | 0.80 | 0.90 | 1.70 |
| 20.00 | 0.80 | 0.91 | 1.71 |
| 21.00 | 0.80 | 0.92 | 1.72 |
| 22.00 | 0.80 | 0.93 | 1.73 |

TABLE 4-continued

| Heart rate threshold (beats per minute) | Sensitivity | Specificity | Sum of Sensitivity and Specificity |
|---|---|---|---|
| 22.75 | 0.70 | 0.93 | 1.63 |
| 25.00 | 0.70 | 0.94 | 1.64 |
| 27.00 | 0.60 | 0.95 | 1.55 |
| 28.00 | 0.50 | 0.95 | 1.45 |
| 29.00 | 0.40 | 0.95 | 1.35 |
| 30.75 | 0.20 | 0.95 | 1.15 |
| 32.00 | 0.10 | 0.95 | 1.05 |
| 33.00 | 0.10 | 0.97 | 1.07 |
| 34.00 | 0.10 | 0.98 | 1.08 |
| 53.00 | 0.00 | 0.98 | 0.98 |
| 56.00 | 0.00 | 0.99 | 0.99 |

It is noted with respect to Table 4 that the greatest sum of sensitivity and specificity is for a heart rate threshold of beats per minute for predicting major adverse clinical events. FIG. 3B shows the ROC curve for a heart rate threshold of 22 with respect to predicting a likelihood of a major adverse clinical event. The area under the curve is 0.79 with a standard deviation of 0.11 and a p-value of 0.0024.

In general, in accordance with the indications provided by the data in Tables 3 and 4 and in FIGS. 3A and 3B, a subject's heart rate is monitored. The median (or mean, or maximum) heart rate over a time duration of more than two hours and less than eight hours (e.g., greater than three hours, greater than four hours, greater than five hours, or greater than six hours) is determined and is compared to the median (or mean, or maximum) heart rate over a similar time duration at a similar period of the day (e.g., at the same time of day) on at least one previous day (e.g., the previous day). In response to determining (a) that the median (or mean, or maximum) heart rate of the present day differs from that of the previous day by a threshold amount of more than 15 beats per minute (e.g., more than 18 beats per minute, e.g., more than 20 beats per minute), and/or less than beats per minute, then an alert is generated in order to indicate that an adverse clinical event is likely to occur.

Table 5 (shown below) shows the results of the ROC curve analysis of respective maximum respiration rate thresholds (i.e., thresholds for the difference between the maximum respiration rate and that of the previous day), with respect to determining the likelihood of a subject undergoing a major or a moderate clinical event.

TABLE 5

| Respiration rate threshold (breaths per minute) | Sensitivity | Specificity | Sum of Sensitivity and Specificity |
|---|---|---|---|
| 0.00 | 1.00 | 0.00 | 1.00 |
| 0.50 | 1.00 | 0.05 | 1.05 |
| 1.00 | 1.00 | 0.06 | 1.06 |
| 1.50 | 1.00 | 0.24 | 1.24 |
| 2.00 | 1.00 | 0.26 | 1.26 |
| 3.00 | 1.00 | 0.43 | 1.43 |
| 3.50 | 1.00 | 0.58 | 1.58 |
| 4.00 | 1.00 | 0.59 | 1.59 |
| 5.00 | 1.00 | 0.70 | 1.70 |
| 6.00 | 0.69 | 0.76 | 1.46 |
| 6.50 | 0.54 | 0.83 | 1.37 |
| 6.75 | 0.54 | 0.85 | 1.39 |
| 7.00 | 0.46 | 0.85 | 1.31 |
| 7.50 | 0.38 | 0.89 | 1.28 |
| 8.00 | 0.31 | 0.89 | 1.20 |
| 9.00 | 0.23 | 0.92 | 1.15 |
| 10.00 | 0.23 | 0.92 | 1.16 |
| 12.00 | 0.23 | 0.93 | 1.16 |
| 16.00 | 0.23 | 0.97 | 1.20 |
| 18.00 | 0.15 | 0.97 | 1.13 |
| 19.00 | 0.08 | 0.98 | 1.06 |
| 24.00 | 0.00 | 0.98 | 0.98 |
| 35.00 | 0.00 | 0.99 | 0.99 |

Figure 3C:
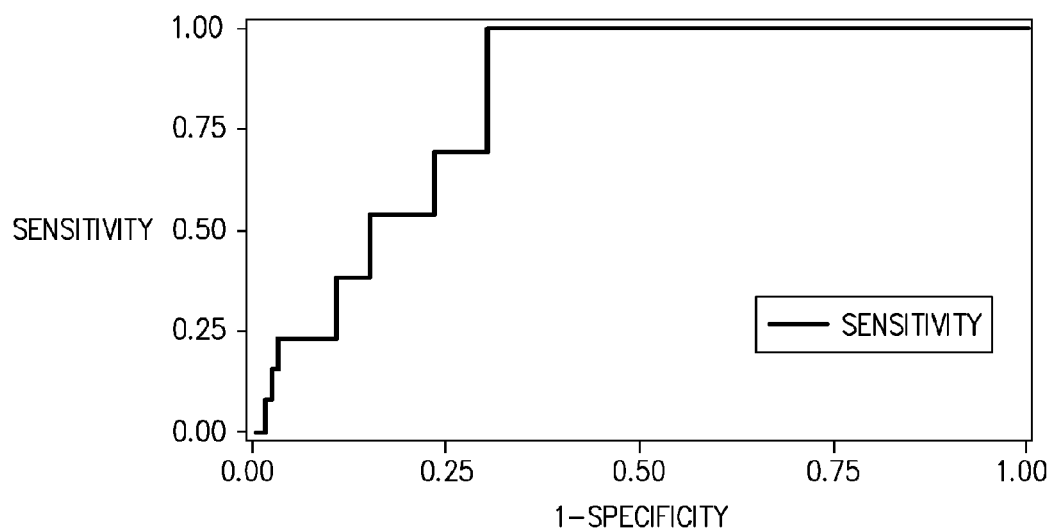

It is noted with respect to Table 5 that the greatest sum of sensitivity and specificity is for a respiration rate threshold of 5 breaths per minute, for predicting major and moderate adverse clinical events. FIG. 3C shows the ROC curve for a respiration rate threshold of 5 with respect to predicting a likelihood of either a major or a moderate adverse clinical event. The area under the curve is 0.84 with a standard deviation of 0.04, and a p-value of 0.000049.

Table 6 (shown below) shows the results of the ROC curve analysis of respective respiration rate thresholds (i.e., thresholds for the difference between the maximum respiration rate and that of the previous day), with respect to determining the likelihood of a subject undergoing a major clinical event.

TABLE 6

| Respiration rate threshold (breaths per minute) | Sensitivity | Specificity | Sum of Sensitivity and Specificity |
|---|---|---|---|
| 0.00 | 1.00 | 0.00 | 1.00 |
| 0.50 | 1.00 | 0.05 | 1.05 |
| 1.00 | 1.00 | 0.06 | 1.06 |
| 1.50 | 1.00 | 0.23 | 1.23 |
| 2.00 | 1.00 | 0.26 | 1.26 |
| 3.00 | 1.00 | 0.42 | 1.42 |
| 3.50 | 1.00 | 0.57 | 1.57 |
| 4.00 | 1.00 | 0.58 | 1.58 |
| 5.00 | 1.00 | 0.69 | 1.69 |
| 6.00 | 0.73 | 0.76 | 1.49 |
| 6.50 | 0.55 | 0.83 | 1.37 |
| 6.75 | 0.55 | 0.84 | 1.39 |
| 7.00 | 0.55 | 0.85 | 1.40 |
| 7.50 | 0.45 | 0.89 | 1.35 |
| 8.00 | 0.36 | 0.89 | 1.26 |
| 9.00 | 0.27 | 0.92 | 1.19 |
| 10.00 | 0.27 | 0.93 | 1.20 |
| 12.00 | 0.27 | 0.93 | 1.21 |
| 16.00 | 0.27 | 0.97 | 1.24 |
| 18.00 | 0.18 | 0.98 | 1.16 |
| 19.00 | 0.09 | 0.98 | 1.07 |
| 24.00 | 0.00 | 0.98 | 0.98 |
| 35.00 | 0.00 | 0.99 | 0.99 |

Figure 3D:
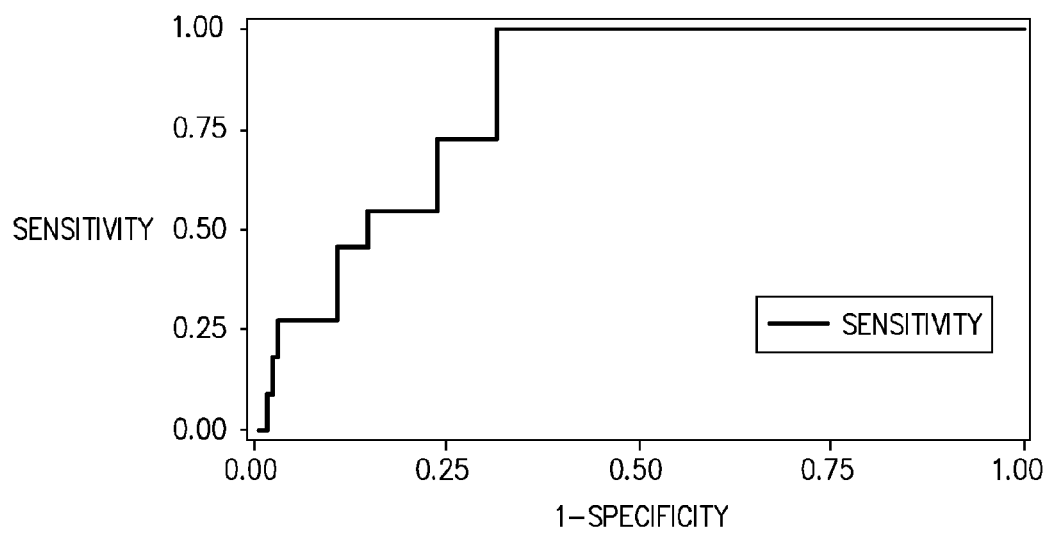

It is noted with respect to Table 6 that the greatest sum of sensitivity and specificity is for a respiration rate threshold of 5 breaths per minute for predicting major adverse clinical events. FIG. 3D shows the ROC curve for a respiration rate threshold of 5 with respect to predicting a likelihood of a major adverse clinical event. The area under the curve is 0.85 with a standard deviation of 0.04, and a p-value of 0.00012.

In general, in accordance with the indications provided by the data in Tables 5 and 6 and in FIGS. 3C and 3D, a subject's respiration rate is monitored. The median (or mean, or maximum) respiration rate over a time duration of more than two hours and less than eight hours (e.g., greater than three hours, greater than four hours, greater than five hours, or greater than six hours) is determined and is compared to the median (or mean, or maximum) respiration rate over a similar time duration at a similar period of the day (e.g., at the same time of day) on at least one previous day (e.g., the previous day). In response to determining (a) that the median (or mean, or maximum) respiration rate of the present day differs from that of the previous day by a threshold amount of more than 3 breaths per minute (e.g., more than 4 breaths per minute), and/or less than 10 breaths per minute (e.g., less than eight, or less than six breaths per minute), then an alert is generated in order to indicate that an adverse clinical event is likely to occur.

For some applications, the techniques described herein are used in combination with the techniques described in one or more of the following references, both of which are incorporated herein by reference:

U.S. Pat. No. 7,077,810 to Lange; and/or
U.S. Pat. No. 7,314,451 to Halperin.

For example, for some applications, as is generally described in U.S. Pat. No. 7,077,810 to Lange, pattern analysis module 22 is configured to predict the onset of an asthma attack or a different clinical event, and/or monitor its severity and progression. Module 22 typically analyzes changes in breathing rate and in breathing rate variability patterns in combination to predict the onset of an asthma attack. Although breathing rate typically slightly increases prior to the onset of an attack, this increase alone is not always a specific marker of the onset of an attack. Therefore, in order to more accurately predict the onset of an attack, and monitor the severity and progression of an attack, module 22 typically additionally analyzes changes in breathing rate variability patterns. For some applications, module 22 compares one or more of the following patterns to respective baseline patterns, and interprets a deviation from baseline as indicative of (a) the onset of an attack, and/or (b) the severity of an attack in progress:

- a slow trend breathing rate pattern. Module 22 interprets as indicative of an approaching or progressing attack an increase vs. baseline, for example, for generally healthy subjects, an attenuation of the typical segmented, monotonic decline of breathing rate typically over at least 1 hour, e.g., over at least 2, 3, or 4 hours, or the transformation of this decline into an increasing breathing rate pattern, depending on the severity of the attack;
- a breathing rate variability pattern. Module 22 interprets as indicative of an approaching or progressing attack a decrease in breathing rate variability. Such a decrease generally occurs as the onset of an episode approaches, and intensifies with the progression of shortness of breath during an attack;
- a breathing duty-cycle pattern. Module 22 interprets a substantial increase in the breathing duty-cycle as indicative of an approaching or progressing attack. Breathing duty-cycle patterns include, but are not limited to, inspirium time/total breath cycle time, expirium time/total breath cycle time, and (inspirium+expirium time)/total breath cycle time; and
- interruptions in breathing pattern such as caused by coughs, sleep disturbances, or waking. Module 22 quantifies these events, and determines their relevance to prediction of potential asthma attacks.

Reference is made to FIG. 4, which is a graph illustrating breathing rate patterns of a chronic asthma patient, and which is the same as FIG. 4 of U.S. Pat. No. 7,077,810 to Lange. Breathing of the asthma patient was monitored during sleep on several nights. The patient's breathing rate was averaged for each hour of sleep (excluding periods of rapid eye movement (REM) sleep). During the first approximately two months that the patient was monitored, the patient did not experience any episodes of asthma. A line 100 is representative of a typical slow trend breathing pattern recorded during this non-episodic period, and thus represents a baseline slow trend breathing rate pattern for this patient. It should be noted that, unlike the monotonic decline in breathing rate typically observed in non-asthmatic patients, the baseline breathing rate pattern of the chronically asthmatic patient of the experiment reflects an initial decline in breathing rate during the first few hours of sleep, followed by a gradual increase in breathing rate throughout most of the rest of the night.

Lines 102 and 104 were recorded on two successive nights at the conclusion of the approximately two-month period, line 102 on the first of these two nights, and line 104 on the second of these two nights. The patient experienced an episode of asthma during the second of these nights. Lines 102 and 104 thus represent a pre-episodic slow trend breathing rate pattern and an episodic slow trend breathing rate pattern, respectively. As can be seen in the graph, the patient's breathing rate was substantially elevated vs. baseline during all hours of the pre-episodic night, and even further elevated vs. baseline during the episodic night.

Using techniques described herein, the pattern of line 102 is compared with the baseline pattern of line 100, in order to predict that the patient may experience an asthmatic episode. The pattern of line 104 is compared with the baseline pattern of line 100 in order to assess a progression of the asthmatic episode.

In accordance with the data shown in FIG. 4, for some applications, a subject's respiration is detected on first and second days over similar time durations and at similar time periods (e.g., during the first two, three four, five, or six hours of the subject's sleep). A parameter of the subject's respiration based upon the detected respiration rate on the second day is compared with that of the first day. An alert is generated in response to the comparison indicating that an adverse clinical event is approaching, e.g., in response to determining that the difference between the median, the mean, and/or the maximum respiration rate on the second day and that of the first day exceeds a threshold.

For some applications, techniques as described in U.S. Pat. No. 7,314,451 to Halperin are used in conjunction with the techniques described herein. For example, for some applications, system 10 monitors and records patterns throughout all or a large portion of a night. The resulting data set generally encompasses typical long-term respiratory and heartbeat patterns, and facilitates comprehensive analysis. Additionally, such a large data set enables rejection of segments contaminated with movement or other artifacts, while retaining sufficient data for a statistically significant analysis.

Although breathing rate typically slightly increases prior to the onset of an asthma attack (or a different adverse clinical event), this increase alone is not always a specific marker of the onset of an attack. Therefore, in order to more accurately predict the onset of an attack, and monitor the severity and progression of an attack, in an embodiment of the present invention, breathing pattern analysis module 22 additionally analyzes changes in breathing rate variability patterns. For some applications, module 22 compares one or more of the following patterns to respective baseline patterns, and interprets a deviation from baseline as indicative of (a) the onset of an attack, and/or (b) the severity of an attack in progress:

- a slow trend breathing rate pattern. Module 22 interprets as indicative of an approaching or progressing attack an increase vs. baseline, for example, for generally healthy subjects, an attenuation of the typical segmented, monotonic decline of breathing rate typically over at least 1 hour, e.g., over at least 2, 3, or 4 hours, or the transformation of this decline into an increasing breathing rate pattern, depending on the severity of the attack;

- a breathing rate pattern. Module 22 interprets as indicative of an approaching or progressing attack an increase or lack of decrease in breathing rate during the first several hours of sleep, e.g., during the first 2, 3, or 4 hours of sleep.
- a breathing rate variability pattern. Module 22 interprets a decrease in breathing rate variability as indicative of an approaching or progressing attack. Such a decrease generally occurs as the onset of an episode approaches, and intensifies with the progression of shortness of breath during an attack;
- a breathing duty-cycle pattern. Module 22 interprets a substantial increase in the breathing duty-cycle as indicative of an approaching or progressing attack. Breathing duty-cycle patterns include, but are not limited to, inspirium time/total breath cycle time, expirium time/total breath cycle time, and (inspirium+expirium time)/total breath cycle time;
- a change in breathing rate pattern towards the end of night sleep (typically between about 3:00 A.M. and about 6:00 A.M.); and
- interruptions in breathing pattern such as caused by coughs, sleep disturbances, or waking. Module 22 quantifies these events, and determines their relevance to prediction of potential asthma attacks.

Pattern analysis modules 22 and 23 typically determine baseline patterns by analyzing breathing and/or heart rate patterns, respectively, of the subject during non-symptomatic nights. Alternatively or additionally, modules 22 and 23 are programmed with baseline patterns based on population averages. For some applications, such population averages are segmented by characteristic traits such as age, height, weight, and gender.

Reference is again made to FIG. 4, which is a graph illustrating breathing rate patterns of a chronic asthma patient, measured during an experiment conducted in accordance with an embodiment of the present invention. Using techniques described herein, breathing pattern analysis module 22 compares the pattern of line 102 with the baseline pattern of line 100, in order to predict that the patient may experience an asthmatic episode. Module 22 compares the pattern of line 104 with the baseline pattern of line 100 in order to assess a progression of the asthmatic episode.

For some applications of the present invention, the deviation from baseline is defined as the cumulative deviation of the measured pattern from the baseline pattern. A threshold indicative of a clinical condition is set equal to a certain number of standard errors (e.g., one standard error). Alternatively or additionally, other measures of deviation between measured and baseline patterns are used, such as correlation coefficient, mean square error, maximal difference between the patterns, and the area between the patterns. Further alternatively or additionally, pattern analysis module 16 uses a weighted analysis emphasizing specific regions along the patterns, for example, by giving increased weight (e.g., double weight) to an initial portion of sleep (e.g., the first two hours of sleep) or to specific hours, for example as morning approaches (e.g., the hours of 3:00-6:00 a.m.).

Figure 7:
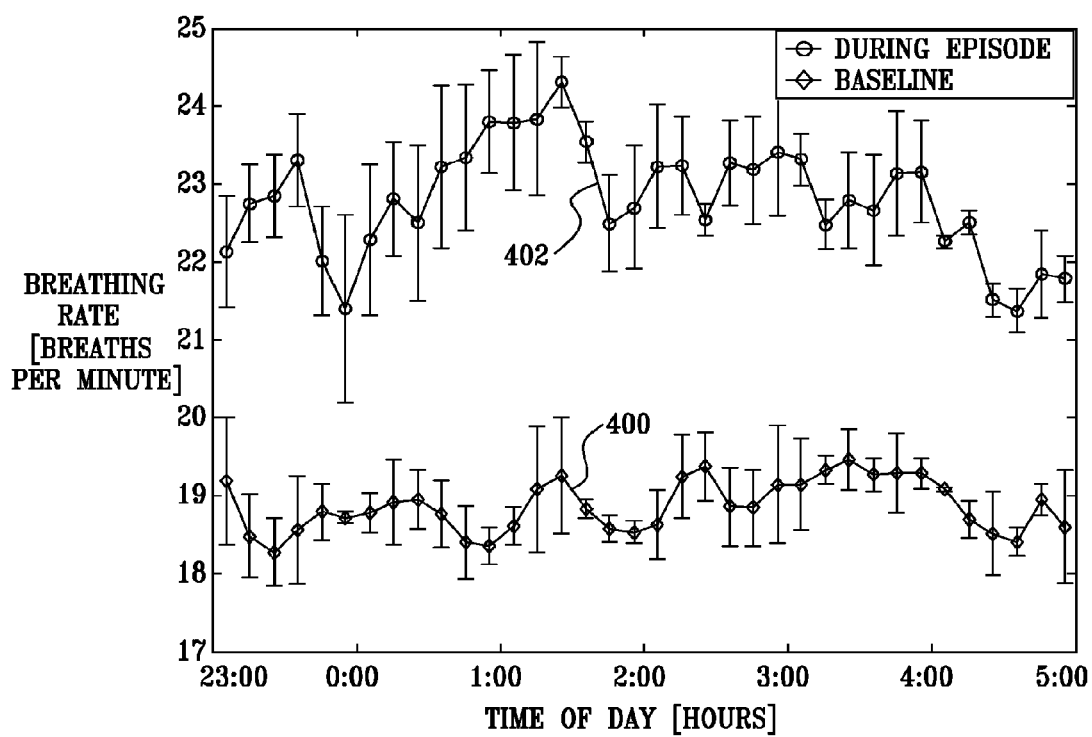
FIG. 7 is a graph of baseline and breathing rate nighttime patterns, respectively, which is the same as FIG. 23 of U.S. Pat. No. 7,314,451 to Halperin.

Reference is now made to FIGS. 5 and 6, which are graphs of exemplary baseline and measured breathing rate and heart rate nighttime patterns, respectively, and which are generally similar to FIGS. 6 and 7 of U.S. Pat. No. 7,314,451 to Halperin, which is incorporated herein by reference. Lines 200 and 202 (FIGS. 5 and 6, respectively) represent normal baseline patterns in the absence of an asthma attack. The bars represent one standard error. Lines 204 and 206 (FIGS. 5 and 6, respectively) represent patterns during nights prior to an onset of an asthma attack. Detection of the change in pattern between lines 200 and 202 and lines 204 and 206, respectively, enables the early prediction of the approaching asthma attack, or other approaching adverse clinical events.

For some applications of the present invention, pattern analysis module 16 is configured to predict the onset of a clinical manifestation of heart failure, and/or monitor its severity and progression. Module 16 typically determines that an episode is imminent when the module detects increased breathing rate accompanied by increased heart rate, and/or when the monitored breathing and/or heartbeat patterns have specific characteristics that relate to heart failure, such as characteristics that are indicative of apnea, Cheyne-Stokes Respiration (CSR), and/or periodic breathing.

In accordance with the data shown in FIG. 5, for some applications, a subject's respiration is detected on first and second days over similar time durations and at similar time periods (e.g., during the first two, three four, five, or six hours of the subject's sleep). A parameter of the subject's respiration based upon the detected respiration rate on the second day is compared with that of the first day. An alert is generated in response to the comparison indicating that an adverse clinical event is approaching, e.g., in response to determining that the difference between the median, the mean, and/or the maximum respiration rate on the second day and that of the first day exceeds a threshold.

In accordance with the data shown in FIG. 6, for some applications, a subject's heart rate is detected on first and second days over similar time durations and at similar time periods (e.g., during the first two, three, four, five, or six hours of the subject's sleep). A parameter of the subject's cardiac cycle based upon the detected heart rate on the second day is compared with that of the first day. An alert is generated in response to the comparison indicating that an adverse clinical event is approaching, e.g., in response to determining that the difference between the median, the mean, and/or the maximum heart rate on the second day and that of the first day exceeds a threshold.

In accordance with the data shown in FIGS. 5 and 6, for some applications, a subject's respiration rate and heart rate are detected on first and second days over similar time durations and at similar time periods (e.g., during the first two, three four, five, or six hours of the subject's sleep). A parameter of the subject's respiration based upon the detected respiration rate on the second day is compared with that of the first day, and a parameter of the subject's cardiac cycle based upon the detected heart rate on the second day is compared with that of the first day. An alert is generated in response to the comparisons indicating that an adverse clinical event is approaching, e.g., in response to determining that (a) the difference between the median, the mean, and/or the maximum respiration rate on the second day and that of the first day exceeds a threshold, and/or (b) the difference between the median, the mean, and/or the maximum heart rate on the second day and that of the first day exceeds a threshold.

Reference is now made to FIG. 7, which is the same as FIG. 23 of U.S. Pat. No. 7,314,451 to Halperin, which is incorporated herein by reference. FIG. 7 is a graph of baseline and breathing rate nighttime patterns, respectively, measured in accordance with some applications of the present invention. A line 400 represents a normal baseline pattern in the absence of Cheyne-Stokes Respiration, and a line 402 represents a pattern during a night during CSR. The bars represent one standard error. In accordance with the data shown in FIG. 7, for some applications, a subject's respiration is detected on first and second days over similar time durations and at similar time periods (e.g., during the first two, three four, five, or six hours of the subject's sleep). A parameter of the subject's respiration based upon the detected respiration rate on the second day is compared with that of the first day. An alert is generated in response to the comparison indicating that an adverse clinical event is approaching, e.g., in response to determining that the difference between the median, the mean, and/or the maximum respiration rate on the second day and that of the first day exceeds a threshold.

For some applications, techniques described herein are used in conjunction with techniques as are generally described in US 2007/0118054 to Pinhas, which is incorporated herein by reference. For example, as is described with reference to FIG. 18 of US 2007/0118054 to Pinhas, for some applications, system 10 is adapted to monitor multiple clinical parameters such as respiration rate, heart rate, cough occurrence, body movement, deep inspirations, expiration/inspiration ratio, of subject 12. Pattern analysis module 16 is adapted to analyze the respective patterns in order to identify a change in the baseline pattern of the clinical parameters. In some cases, this change, a new baseline that is significantly different from the previous baseline indicates, for example, a change in medication and provides the caregiver or healthcare professional with feedback on the efficacy of treatment.

For some applications, system 10 calculates the average respiration rate and heart rate for predefined time segments. Such time segments can be minutes, hours, or days. By analyzing the history of the patient the system can calculate the correlation of respiration rate and heart rate patterns. When an onset of an asthma attack approaches the correlation of heart rate and respiration rate pattern shows a clear change. For each night the respiration rate and heart rate in sleep during the hours of 11:00 pm to 6:00 am (or over a different time period) is averaged. For each date, a respiration vector of length N with the average respiration rate of the last N nights and a heart rate vector of length N with the average heart rate for the last N nights is defined. N is typically between 3 and 30, for example 10. The correlation coefficient of the heart rate vector and the respiration vector is calculated for each date by system 10. A moving window of several days is used to calculate correlation coefficient changes between the respiration and heart rate vectors. A steady correlation coefficient pattern over at least several days is required to identify a significant change of correlation coefficient from one time interval to another. A significant change is defined as a change in the correlation coefficient level of a magnitude larger than the typical correlation coefficient variation in the previous time interval, e.g., a change larger than 3 standard deviations of the correlation coefficient signal in the previous time interval. System 10 identifies such a significant change as an indication of an approaching clinical event.

As described in US 2007/0118054 to Pinhas, for some applications, during sleep, sleep stage is identified using techniques described therein. For each identified sleep stage, the average respiration rate, heart rate and other clinical parameters are calculated. This data is compared to baseline defined for that subject for each identified sleep stage, in order to identify the onset or progress of a clinical episode.

For some applications, for each night, for each hour (or for longer durations of time, such as more than two hours, as described hereinabove) of sleep, counted from the onset of sleep, the average respiration rate, heart rate and other clinical parameters are calculated. This data is compared to baseline in order to identify the onset or progress of a clinical episode.

For some applications, for each night, for each hour (or for longer durations of time, such as more than two hours, as described hereinabove), the average respiration rate, heart rate and other clinical parameters are calculated. This data is compared to baseline in order to identify the onset or progress of a clinical episode. For example, the average respiration rate in sleep during 2:00 AM-3:00 AM is calculated and compared to baseline for that subject in order to identify the onset or progress of a clinical episode.

Figure 8:
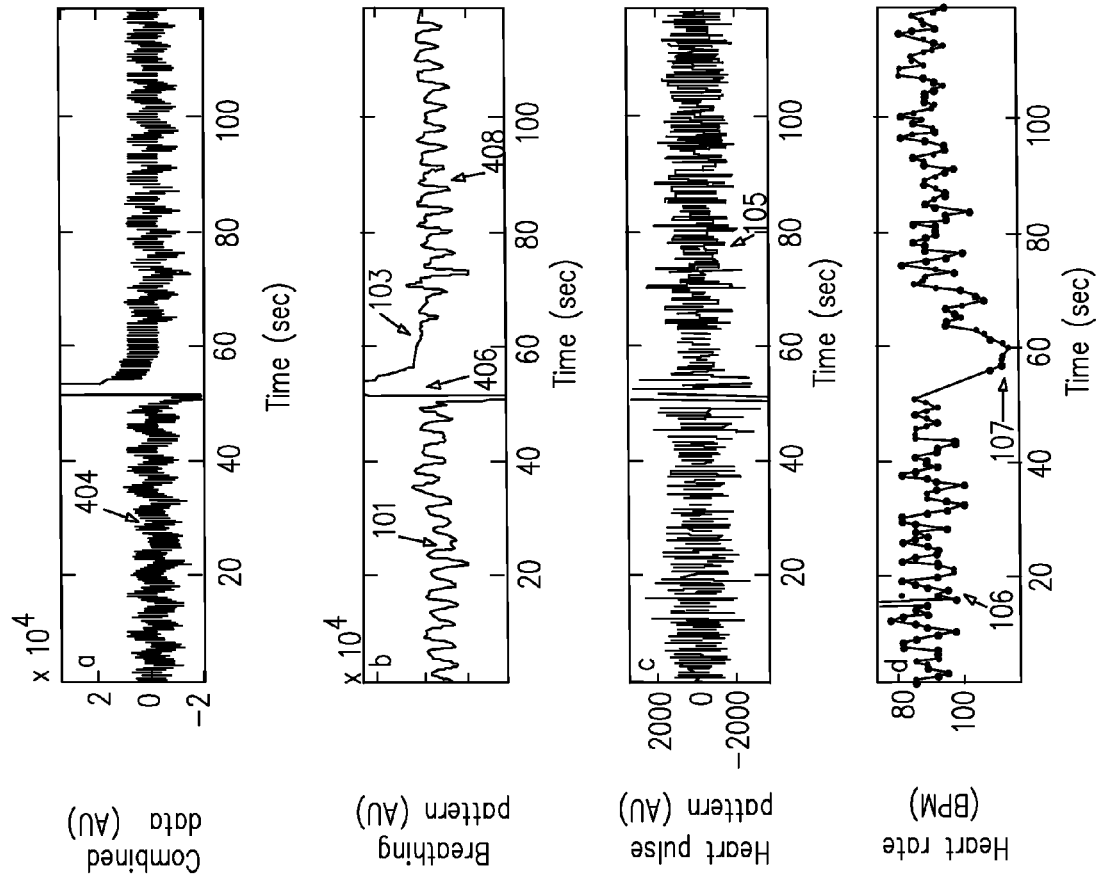
FIGS. 8A-D are graphs illustrating data related to an event of central sleep apnea as measured and analyzed in some applications of the present invention.

In an embodiment of the present invention, system 10 is adapted to monitor breathing and pulse (or heartbeat) patterns in order to recognize Central Sleep Apnea (CSA) episodes. FIGS. 8A-D illustrate an example of a CSA episode, as recorded by system 10, obtained from a 7-year-old asthmatic patient during the night. FIG. 8A shows the combined breathing and pulse signals (line 404), for example, as detected by motion sensor 30 in FIGS. 1 and 2. The corresponding breathing pattern extracted from the combined signal 404 is shown in FIG. 8B. Note that the quiet and steady breathing pattern 101 is followed by a single deep breath cycle 406 and then a 18.7 second interval with no breathing effort, epoch 103, and finally, the breathing pattern returns to normal, epoch 408. Line 105 in FIG. 8C denotes the heart pulse or heartbeat signal derived from the combined signal 404 shown in FIG. 8A. The corresponding beat-to-beat heart rate is shown in FIG. 8D and denoted by line 106. Note the immediate decrease in heart rate during the CSA episode, epoch 107.

Obstructive sleep apnea (OSA) is a disorder in which complete or partial obstruction of the airway during sleep occurs due to a collision of the pharynx into the upper airway that blocks breathing. As a result, the patient suffers from loud snoring, oxyhemoglobin desaturations, and frequent arousals. These arousals may occur hundreds of times each night but do not fully awaken the patient, who remains unaware of the loud snoring, choking, and gasping for air that are typically associated with obstructive sleep apnea. In contrast to central sleep apnea, OSA includes futile inspiratory efforts.

Figure 9:
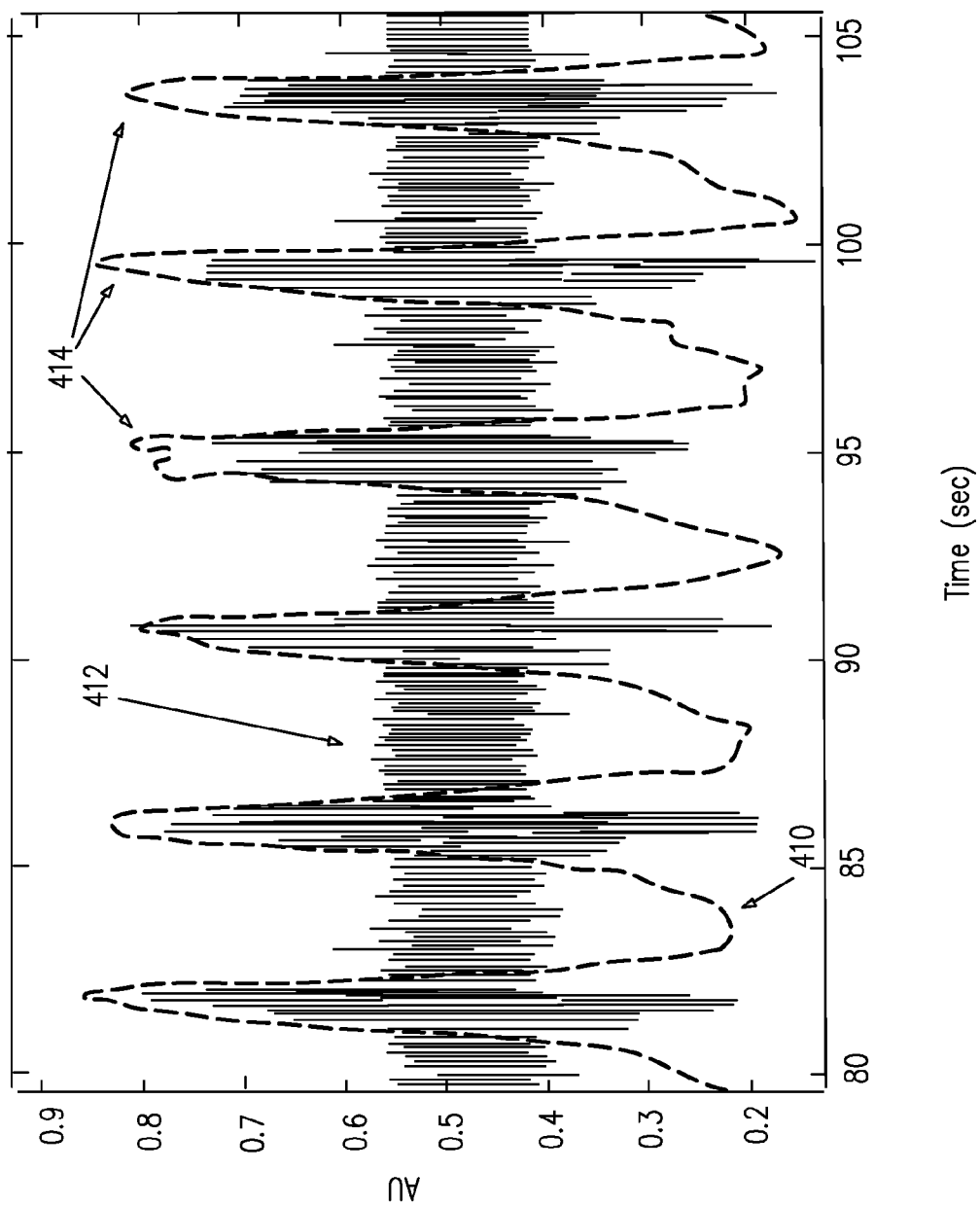
FIG. 9 is a graph illustrating motion and acoustic data as measured and analyzed in some applications of the present invention.

In one embodiment, system 10 monitors breathing patterns through the mechanical channel and the acoustic or audio signals, for example, snoring, through the audio channel. Snoring is identified as a significant acoustic signal that is time correlated with the breathing pattern. The system recognizes epochs, that is, time periods, that include loud snoring. The system marks events as partial OSA when the audio signal decreases although the breathing effort remains constant or even increases. FIG. 9 shows an example of partial OSA as recorded by the system, obtained from an 8-year-old asthmatic patient during the night. Line 410 in FIG. 9 denotes the breathing pattern and line 412 denotes the associated audio signal. The breathing efforts in the last 3 cycles, 414, are similar to the efforts in the first 3 cycles, whereas the audio amplitude in the last 3 cycles, 414, are significantly decreased compared to the audio amplitude during the first 3 cycles. In one embodiment, system 10 also monitors the heart rate simultaneously with the above and verifies a suspicious apnea event by looking for the characteristic change in heart rate.

In one embodiment, the system monitors breathing patterns through the mechanical channel and snoring through the audio signal. The system recognizes increasing respiratory motion with decreasing audio signal leading up to a restlessness event. The system identifies this pattern as a probable OSA pattern.

In one embodiment of the present invention, the system identifies the recurring pattern of OSA or CSA for the subject and identifies the pattern that precedes the apnea event, for example, the gradually decreasing amplitude of the respiration motion before CSA in a patient suffering from Cheyne Stokes Respiration (CSR) or the initial labored breathing with reduced audio signal of OSA or the deep inspiration before CSA. Upon identifying the pattern that precedes the apnea event, system 10 immediately activates a therapeutic device to prevent the apnea event from taking its full course. The therapeutic device can be, for example, a Continuous Positive Airway Pressure (CPAP) system which is placed on the patient's face continuously but only activated on an as needed basis. Once the respiration pattern returns to normal, or the apnea at least subsides, and the therapeutic device is no longer needed, system 10 turns off the therapeutic device until the next oncoming apnea event is identified. In such a way the system prevents apnea events while not having to constantly operate the therapeutic device which may make falling asleep more difficult or have other side effects.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A method of predicting an onset of apnea, the method comprising:
    sensing motion of a subject without contacting the subject, the motion comprising motions related to at least breathing, and generating a signal corresponding to the sensed motion;
    extracting a breathing-related signal from the sensed motion signal; and
    predicting the onset of apnea at least partially in response to analyzing the breathing-related signal.

2. The method according to claim 1, wherein the motion further comprises motions related to heartbeat, wherein the method further comprises extracting a heartbeat-related signal from the sensed motion signal, and wherein predicting the onset of apnea is at least partially in response to analyzing the heartbeat-related signal.

3. The method according to claim 1, wherein the method is practiced without requiring compliance of the subject.

4. The method according to claim 1, wherein the method further comprises treating the subject for apnea when the onset of apnea is predicted.

5. A system for predicting an onset of apnea, the system comprising:
    at least one sensor adapted to:
        sense motion of a subject without contacting the subject, the sensed motion comprising motions related to at least breathing, and
        generate a signal corresponding to the sensed motion; and
    an analyzer adapted to:
        extract a breathing-related signal from the sensed motion signal, and
        analyze the breathing-related signal to predict the onset of apnea.

6. The system according to claim 5, wherein the sensed motion further comprises motions related to heartbeat, and wherein the analyzer is further adapted to:
    extract a heartbeat-related signal from the sensed motion signal, and
    analyze the heartbeat-related signal to predict the onset of apnea.

7. The system according to claim 5, wherein the system further comprises an apnea treatment device that is activated when the onset of apnea is predicted.

8. A method of detecting an onset of apnea, the method comprising:
    sensing an audio signal near a subject;
    sensing breathing of the subject without contacting the subject and generating a breathing-related signal corresponding to the sensed breathing; and
    analyzing the audio signal and the breathing-related signal to detect the onset of apnea.

9. The method according to claim 8, wherein the analyzing comprises detecting a decrease in amplitude of the audio signal and correlating the decrease with little or no decrease in amplitude of the breathing-related signal.

10. The method according to claim 8, wherein the method is practiced during periods of snoring.

11. The method according to claim 8, wherein the method further comprises, following detection of the onset of apnea, activating a therapeutic device to at least reduce the apnea.

12. The method according to claim 11, wherein the method further comprises deactivating the therapeutic device when the apnea subsides.

13. The method according to claim 8, wherein the method is practiced without contacting or viewing clothes the subject is wearing.

14. The method according to claim 8, wherein the method is practiced without requiring compliance of the subject.

15. Apparatus for detecting an onset of apnea, the apparatus comprising:
    an audio sensor adapted to sense sound from a subject and generate an audio signal corresponding to the sensed sound;
    at least one sensor adapted to sense breathing of the subject without contacting the subject and generate a breathing-related signal corresponding to the sensed breathing; and
    an analyzer adapted to analyze the audio signal and the breathing-related signal to detect the onset of apnea.

16. The apparatus according to claim 15, wherein the analyzer is adapted to detect a decrease in amplitude of the audio signal and correlate the decrease with little or no decrease in amplitude of the breathing-related signal.

17. The apparatus according to claim 15, wherein the audio sensor is adapted to detect snoring.

18. The apparatus according to claim 15, wherein the apparatus further comprises a therapeutic device and means for activating the therapeutic device when the onset of apnea is detected.

19. The apparatus according to claim 18, wherein the apparatus further comprises means for deactivating the therapeutic device when the apnea subsides.

* * * * *